US006790198B1

(12) United States Patent
White et al.

(10) Patent No.: US 6,790,198 B1
(45) Date of Patent: Sep. 14, 2004

(54) PATIENT MEDICATION IV DELIVERY PUMP WITH WIRELESS COMMUNICATION TO A HOSPITAL INFORMATION MANAGEMENT SYSTEM

(75) Inventors: Gale White, Fort Worth, TX (US); Roger Hill, Richardson, TX (US); Michael J. Zakrewski, Carrollton, TX (US); Ruth Kummerlen, Frisco, TX (US); Martyn Stuart Abbott, Dallas, TX (US); Robert C. Brooks, Mabank, TX (US)

(73) Assignee: B-Braun Medical, Inc., Carrollton, TX (US)

( * ) Notice: Subject to any disclaimer, the term of this patent is extended or adjusted under 35 U.S.C. 154(b) by 552 days.

(21) Appl. No.: 09/702,310

(22) Filed: Oct. 31, 2000

Related U.S. Application Data

(63) Continuation-in-part of application No. 09/452,488, filed on Dec. 1, 1999, now Pat. No. 6,519,569.

(51) Int. Cl.[7] .................................................. A61M 1/00
(52) U.S. Cl. ............................. 604/151; 604/67; 705/3; 700/237
(58) Field of Search .............................. 604/65, 66, 67, 604/151; 128/DIG. 12, DIG. 13, 903, 904; 235/375

(56) References Cited

U.S. PATENT DOCUMENTS

| 4,308,866 A | 1/1982 | Jelliffe et al. ............... 128/214 |
| 4,373,527 A | 2/1983 | Fischell ...................... 128/260 |
| 4,443,218 A | 4/1984 | DeCant, Jr. et al. .......... 604/67 |
| 4,476,381 A | 10/1984 | Rubin |
| 4,543,955 A | 10/1985 | Schroeppel ................. 128/635 |
| 4,573,994 A | 3/1986 | Fischell et al. |
| 4,706,207 A | 11/1987 | Hennessy et al. |
| 4,731,051 A | 3/1988 | Fischell ....................... 604/67 |
| 4,756,706 A | 7/1988 | Kerns et al. .................. 604/66 |
| D297,939 S | 10/1988 | Bradbury et al. |
| 4,814,759 A | 3/1989 | Gombrich et al. |
| 4,818,850 A | 4/1989 | Gombrich et al. |
| 4,831,562 A | 5/1989 | McIntosh et al. |
| 4,835,372 A | 5/1989 | Gombrich et al. .......... 235/375 |
| 4,847,764 A | 7/1989 | Halvorson ............. 364/413.02 |
| 4,850,009 A | 7/1989 | Zook et al. |
| 4,853,521 A | 8/1989 | Claeys et al. |
| 4,857,713 A | 8/1989 | Brown |
| 4,857,716 A | 8/1989 | Gombrich et al. .......... 235/462 |
| 4,916,441 A | 4/1990 | Gombrich .................. 340/712 |
| 4,925,444 A | 5/1990 | Orkin et al. |
| 4,978,335 A | 12/1990 | Arthur, III |

(List continued on next page.)

OTHER PUBLICATIONS

AcuDose–Rx, For storing, dispensing and tracking narcotic, floorstock and PRN medication, McKessonHBOC, Automated Healthcare.

(List continued on next page.)

*Primary Examiner*—Manuel Mendez
(74) *Attorney, Agent, or Firm*—John W. Montgomery

(57) ABSTRACT

A wireless communication system from an IV medication infusion pump to a hospital information management system (HIMS) is disclosed. The system includes an IV pump having pump operation circuitry for monitoring preselected characteristics of pump operation indicative of IV administration of medication to a patient. A transmitter is connected to the pump operation circuitry for transmitting a wireless pump signal representing the preselected pump operation characteristics. The wireless pump transmitter communicates with a hospital information management system (HIMS). The HIMS includes a receiver capable of receiving the pump signal representing the pump operation characteristics and also includes a computer capable of storing and displaying the pump operation characteristics represented by the received wireless pump signal.

21 Claims, 6 Drawing Sheets

U.S. PATENT DOCUMENTS

| | | |
|---|---|---|
| 5,006,699 A | 4/1991 | Felkner et al. |
| 5,049,047 A | 9/1991 | Polaschegg et al. ........ 417/474 |
| 5,104,374 A | 4/1992 | Bishko et al. |
| 5,153,416 A | 10/1992 | Neeley |
| 5,153,827 A | 10/1992 | Coutre et al. |
| 5,179,569 A | 1/1993 | Sawyer |
| 5,207,642 A | 5/1993 | Orkin et al. |
| 5,213,483 A | 5/1993 | Flaherty et al. ............. 417/477 |
| 5,272,318 A | 12/1993 | Gorman |
| 5,307,372 A | 4/1994 | Sawyer et al. |
| 5,317,506 A | 5/1994 | Coutré et al. .......... 364/413.02 |
| 5,319,363 A | 6/1994 | Welch et al. .......... 340/825.36 |
| 5,348,008 A | 9/1994 | Bornn et al. |
| 5,368,562 A | 11/1994 | Blomquist et al. ............ 604/65 |
| 5,373,527 A | 12/1994 | Taniu et al. .................. 372/71 |
| 5,374,813 A | 12/1994 | Shipp |
| 5,378,231 A | 1/1995 | Johnson et al. |
| 5,392,638 A | 2/1995 | Kawahara .................. 73/61.49 |
| 5,416,695 A | 5/1995 | Stutman et al. ........ 364/413.02 |
| 5,536,084 A | 7/1996 | Curtis et al. ........... 364/413.01 |
| 5,544,661 A | 8/1996 | Davis et al. ................ 128/700 |
| 5,564,429 A | 10/1996 | Bornn et al. |
| 5,626,151 A | 5/1997 | Linden ...................... 128/897 |
| 5,630,710 A | 5/1997 | Tune et al. ................. 417/326 |
| 5,640,301 A | 6/1997 | Roecker et al. |
| 5,643,212 A | 7/1997 | Coutré et al. ............... 604/131 |
| 5,713,856 A | 2/1998 | Eggers et al. |
| 5,735,263 A | 4/1998 | Rubsamen et al. |
| 5,781,442 A | 7/1998 | Engleson et al. ...... 364/478.02 |
| 5,800,383 A | 9/1998 | Chandler et al. ...... 364/478.02 |
| 5,800,387 A | 9/1998 | Duffy et al. .................. 604/65 |
| 5,840,026 A | 11/1998 | Uber, III et al. |
| 5,871,465 A | 2/1999 | Vasko |
| 6,031,621 A | 2/2000 | Binder |
| 6,070,761 A | 6/2000 | Bloom et al. |
| 6,078,273 A | 6/2000 | Hutchins et al. .............. 341/13 |
| 6,408,330 B1 * | 6/2002 | DeLaHuerga ............... 709/217 |
| 6,477,424 B1 * | 11/2002 | Thompson et al. ........... 607/60 |
| 6,493,747 B2 | 12/2002 | Simmon et al. |
| 6,507,868 B2 | 1/2003 | Simmon et al. |
| 2001/0044731 A1 | 11/2001 | Coffman et al. |

OTHER PUBLICATIONS

AcuDose–Rx, Secure Medication Dispensing Cabinets for Patient Care Areas, McKessonHBOC, Automated Healthcare.

PowerChart, Electronic Medical Record System, Cerner.

AcuScan–RX, Bedside Scanner to Ensure Medication Administration Accuracy, McKessonHBOC, Automated Healthcare.

Electronic Medication Administration Record, Reduce the Risk of Medication Errors with Cerner's Electronic MAR, Cerner/CareNet.

Discern Expert, Cerner, 1997 Cerner Corporation.

* cited by examiner

PATIENT MEDICATION IV DELIVERY PUMP WITH WIRELESS COMMUNICATION TO A HOSPITAL INFORMATION MANAGEMENT SYSTEM

CROSS-REFERENCE TO RELATED APPLICATIONS

This is a continuation-in-part of co-pending application titled "Improved Security Infusion Pump With Bar Code Reader," Ser. No. 09/452,488, filed Dec. 1, 1999, relied upon for priority and incorporated herein by reference.

TECHNICAL FIELD OF THE INVENTION

The present invention relates to an intravenous (IV) infusion pump used in a health care facility such as a hospital, the pump is designed to provide enhanced monitoring and record keeping of infusion pump operations and operational characteristics, such as settings, parameters, conditions or states, through a hospital information management system (HIMS).

BACKGROUND OF THE INVENTION

In hospitals there is a need to accurately monitor the administration of medications to patients. Presently systems for administration of IV medications to a patient in a hospital vary from hospital to hospital in certain specific aspects. However, many basic procedures and practices are similar in a significant number of hospitals for the administration of medications. For example, the administration of medication to a patient originate with prescribed medications ordered by a doctor. The doctor's order is provided to a pharmacy where a trained pharmacist will obtain and prepare the ordered medication. In the case of medications to be administered orally (as with pills), intramuscularly (as with a needle and syringe) or intravenously (as with a mixture of medication in a diluent) the pharmacist may provide the medication for delivery to the patient's nurse with appropriate instructions for administering the medication to the patient according to the doctor's order.

In the case of pills or injections, the pharmacist delivers the pills or a vile for the injection with instructions for the quantity or the amount to be administered.

In the case of an IV medication, the pharmacist prepares an IV solution according to the doctor's order. Typically the resulting IV solution is prepared in a sterile bag in the form of a diluent and the active medication. Often the diluent includes glucose in water for hydrating and nourishing the patient. Other medications may also be included as may facilitate medical treatment.

In the case of a blood product that requires IV administration, the doctor's order is usually be provided to a hospital lab. Where the hospital lab prepares a blood product for administration to a patient. The blood product will typically be provided in a sterile IV hanging bag.

A prepared IV medication solution or blood product is labeled; identifying the patient, identifying the medication (or the blood product) and indicating the appropriate administration instructions according to the Doctor's order. The non-IV medication, the IV medication or the blood product is then delivered to the hospital floor where the patient is residing. Typically all medication goes to a nurses's station on the designated floor and the nurse assigned to the patient administers and documents the administration of the medication.

In the past, monitoring each step of the process from the doctor's order to the pharmacist, to preparation of the medication, to the laboratory preparation of the blood product and to the administration to the patient was by handwritten or typed documentation. The doctor, the pharmacy, the lab and the nurse who actually administers the medication to the patient made separate entries.

The record of medication administration to the patient by the nurse might be a single entry on the patient's chart at the time the medication is given. In the case of oral or intramuscular medications, this record might be sufficient. In the case of an IV medication the administering event actually occurs over an extended period of time during which numerous situations could interfere with complete administration of the medication to the patient and the single event entry may be inadequate.

Modern hospitals have developed central systems using sophisticated computer equipment to help keep track of patients and to monitor the health care services provided to them. These systems including central computer monitoring are sometimes known as Hospital Information Management Systems (HIMS). Typically a patient is given a unique patient identification number when admitted to the hospital. This number is placed on the patient's chart and often on a patient ID bracelet. Selected information known at the time of patient admission to the hospital, for example, information relevant to the patient, the patient's physician, the method of payment or insurance coverage, the patient's condition, initial diagnosis, intended treatment and etc. can be entered into the HIMS at the admissions desk. Other information that might become known or that subsequently becomes relevant during the hospital stay might also be entered into a properly programed HIMS. The HIMS presents possibilities for allowing beneficial information retrieval by authorized healthcare providers in the hospital, whether it be the attending physician, the ER doctors, "on call" physicians, nurses, pharmacist, lab technicians and etc. Portions of the information that is relevant to financial operations such as cost of medications, supplies and special services associated with the patient's care can also be stored and coded for the particular patient and accessed by billing clerks, insurance administrators, and account coordinators, under appropriate access codes or other procedures for maintaining patient privacy.

Much of the patient information is currently typed into the computer through network computer terminals wired to the HIMS. It is difficult to keep certain types of information current, particularly specific patient care information from the patient's hospital room chart. The lag time between providing the care or medication to the patient, writing it on the chart and then entering the charted information into the HIMS at a designated network computer or a data entry terminal often entails a significant delay. Also, appropriately tracking the hospital's inventory and patient use of medications and controlled substances such as addictive drugs is not as current or as accurate as might be hoped.

Modern healthcare, particularly in hospitals, clinics and other healthcare institutions, has improved and benefited significantly from the development and use of medical infusion pumps to enhance patient care. For example, parenteral infusion and, in particular, intravenous infusion directly into the patient's circulatory system, can be advantageous. Therapeutic fluids, drugs, medications, pharmacological fluids, hydrating fluids, sucrose fluids, nutrient fluids, or other therapeutic fluids can generally be infused using disposable cassette pumps and peristaltic pumps. Syringe pumps can also be used in some instances. Particularly, it is advantageous to provide different kinds of controlled infusion including rate controlled infusion, periodic infusion, and bolus dosage infusion, all depending upon the medication, the patient, the patient's condition and any of a number of other healthcare considerations.

In institutional healthcare facilities, such as major hospitals, large clinics and other large medical facilities, prescribed medications are prepared in a facility pharmacy by a staff pharmacist or a team of pharmacists, according to a doctor's order. Detailed instructions for the administration of the drug may also be provided with the prescribed medication to nurses or other highly trained medical professionals according to the doctor's order and according to professional knowledge of the pharmacist with respect to pharmacological protocol for the medication, therapeutic fluids or mixtures of drugs involved. The medication is received by a nurse or a medical professional in an appropriate container prepared by the pharmacist to be delivered to the patient's room and accordingly administered to the patient. For purposes of accurate infusion, rather than merely using a timed drip-type infusion mechanism, infusion pumps are beneficially used. Based upon the prescribed medication, the protocol for administering the modern infusion therapeutic fluid may include carefully controlled infusion rates. Modem infusion pumps maybe adjustably configured by the person administering the infusion to deliver the fluid according to the doctor's and/or pharmacist's instructions.

SUMMARY OF THE INVENTION

A wireless communication system from an IV medication infusion pump to a hospital information management system (HIMS) is disclosed. The system includes an IV pump having pump operation circuitry for monitoring preselected characteristics of pump operation indicative of IV administration of medication to a patient. A transmitter is connected to the pump operation circuitry for transmitting a wireless pump signal representing the preselected pump operation characteristics. The wireless pump transmitter communicates with a hospital information management system (HIMS). The HIMS includes a receiver capable of receiving the pump signal representing the pump operation characteristics and also includes a computer processor capable of storing and displaying the pump operation characteristics represented by the received wireless pump signal.

BRIEF DESCRIPTION OF THE DRAWINGS

The foregoing objects, advantages, and features, as well as other objects and advantages, will become more apparent with reference to the description and drawings below, in which like numerals represent like elements and in which.

DETAILED DESCRIPTION OF THE PREFERRED EMBODIMENTS

Figure 1:
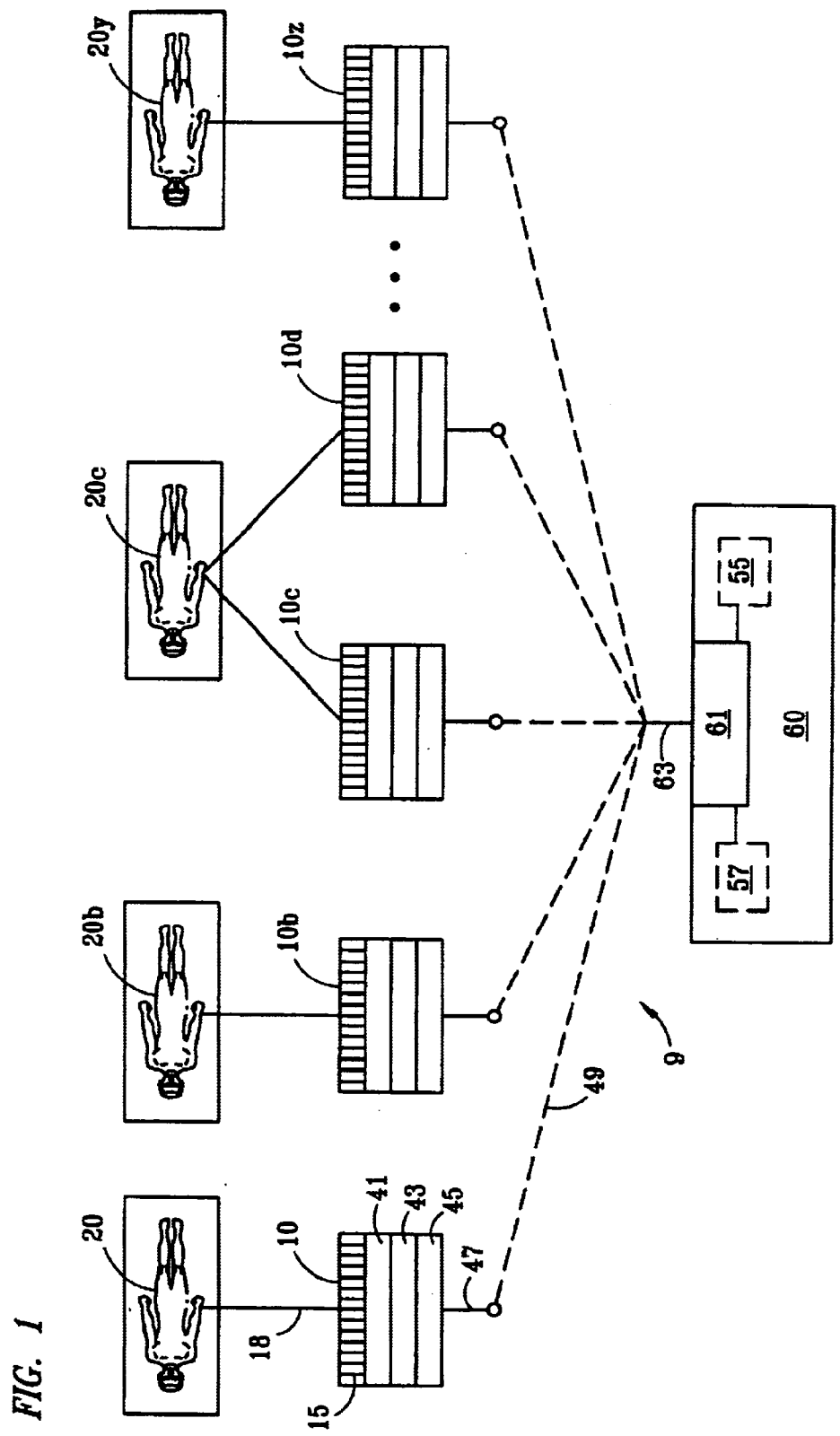
FIG. 1 is a schematic depiction of a hospital system with a plurality of IV pumps with wireless transmission to an HIMS.

A wireless communication system 9 is shown schematically in FIG. 1, permitting wireless signal communication from an IV medication infusion pump 10 to a health care facility information center such as a hospital information management system (HIMS) 60. The system includes at least one IV pump 10 having pump operation circuitry 41 and circuitry 43 for monitoring preselected characteristics 15 of pump operation indicative of IV administration 18 of medication to a patient 20. A transmitter 45 is connected to the IV pump operation circuitry 41 for transmitting a wireless pump signal 49 representing the preselected pump operation characteristics 15. Such pump operation characteristics might include any one or more of pump settings, parameters, conditions, states or changes thereof The wireless pump transmitter 45 wirelessly transmits the pump operation characteristics 15 to the HIMS 60. The HIMS includes a receiver 61 capable of receiving the pump signal 49 representing the pump operation characteristics 15. The HIMS may also include a computer processor 57 capable of storing and displaying at 63 the pump operation characteristics 15 represented by the received wireless pump signal 49.

FIG. 1 also depicts an embodiment comprising a plurality of IV pumps 10, 10b, 10c, 10d, and . . . 10z providing IV medication infusion to a plurality of patients 20, 20b, 20c, 20d, and . . . 20y. It will be understood from the disclosure that any number of pumps 10 may be included in the hospital system for IV infusion to any number of patients 20. Also more than one pump may be provided for any one of the patients. Each of the wireless infusion pumps shall be identified with a unique pump ID such as an identification code, a wireless signal identifier or a digital "address." Similarly, each patient is individually identified with a patient ID for proper security and tracking in the HIMS. Thus each of the plurality of IV pumps can wirelessly communicate with the HIMS and the information regarding the particular pump can be identified and information from the pump regarding the particular patient to whom the identified pump is infusing can be properly identified and tracked in the HIMS. The separate signals are schematically represented as wireless signals 49, 49b, 49c, 49d, and . . . 49z from each pump to the receiver 61 of the HIMS 60. In the embodiment depicted the wireless signal is depicted as being transmitted for a radio frequency (RF) signal from an antenna 47b at the pump 10 to an RF antenna 63 at he HIMS. It will be understood from the disclosure that while an RF wireless signal is advantageously contemplated as the best mode of the invention, other wireless signals such as infrared (IR), laser beam, ultrasonic might be used according to some of the aspects of the invention.

Figure 2:
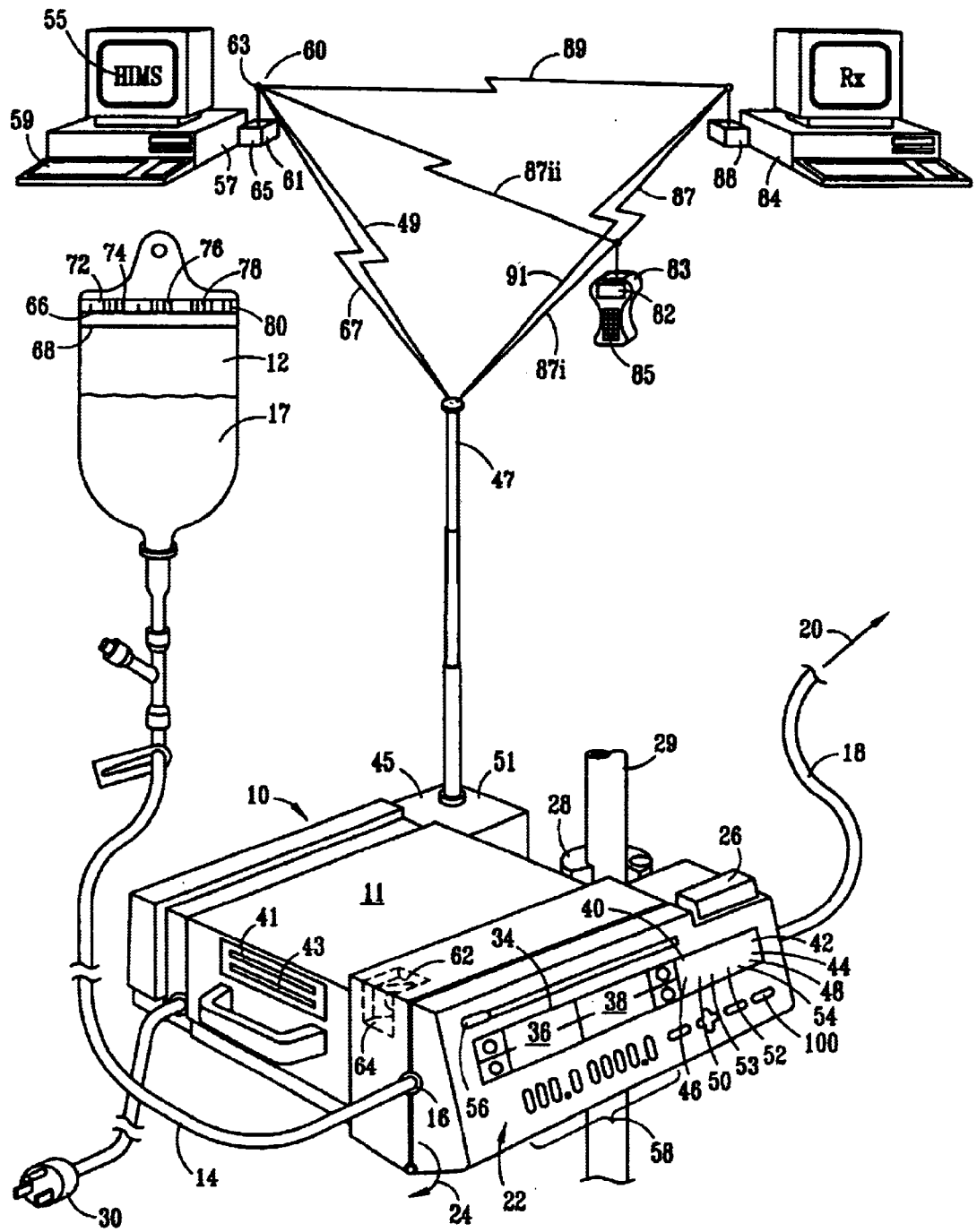
FIG. 2 is a schematic perspective view of an infusion pumping device having a wireless signal transmitter according to one embodiment of the present invention.

FIG. 2 shows a schematic perspective view of an infusion pump 10 according to one aspect of the present invention. In this embodiment the pumping device 10 and its various components are generally enclosed within a housing 11. The pumping device works together with a medicinal fluid 17 to be pumped provided from a container 12 that may be a medical bottle or disposable fluid bag or other container capable of holding the required medicinal fluid and appropriately interfacing with the pumping device 10 to provide the fluid to the patient. Fluid 17 from the container 12 is provided through input tube 14 that may be appropriate plastic or medical grade PVC or silicon tubing. Although a cassette pump is depicted in FIG. 1, it will be understood that principles of wireless transmission of pumping information from an IV pump to an HIMS, according to the present invention, may similarly be applicable to a peristaltic pump or other appropriate infusion pumps or alternative modes of IV pumping. The tubing 14 carries the fluid into the pumping device through access opening 16 that may lead to a disposable pumping cassette as set forth and described in U.S. Pat. No. 5,302,093 and 5,554,013 incorporated by reference herein or alternatively, may be engaged in a peristaltic pumping mechanism such as the linear peristaltic pumping mechanism as disclosed in U.S. Pat. No. 5,660,529 and 5,888,052, also incorporated herein by reference. As the fluid 17 is actively moved through the pump 10, it is carried through an IV tubing 18 to a patient 20, schematically represented by arrow 20 in FIG. 2. Control of the pumping rate, pumping volume, pumping time and safety limitations is generally addressed through a control panel 22. The control panel 22, in FIG. 2, is hingably connected and swings open as indicated by a broken arrow at hinge 24. This allows the pump to accept an administration set attached by tube 14 to IV container 12(or in the case if a peristaltic pump, openable to accept and engage the tubing 14 directly into the peristaltic pumping mechanism). The pump door hinged at 24 is released using a release lever 26. The entire IV pumping mechanism is shown attached through a pole clamp 28 to a pump mounting pole 29. Other modes of supporting the pump can be used. The pump is provided with power, preferably electrical power, schematically represented as an electrical plug 30. Other types or sources of power, such as battery power may be used. For example, a battery back-up system might be appropriately included within the pump for maintaining operations and/or for maintaining stored data or transmitting an alarm condition signal, transmitting pump operational information, operational log data or other data stored at the IV pump 10.

The IV pump 10 is provided with a visual display panel 34 that is conveniently and advantageously formed on the control panel 22. This control panel 22 is provided with a visual display panel 34 to visually show selectably entered adjustable pump operational characteristics and characteristics . For example, but without limiting the nature of the display panel 34 to a particular configuration, separate displays or sectioned display areas might include infusion rate display 36, volume to be delivered display 38 and program infusion data display 40. Monitoring circuitry 41 is provided connected to the pump operation circuitry 43. The monitoring circuitry 41 may provide information for the program infusion display 40 and also for wireless transmission to the HIMS 60. The program infusion data display 40 may include capabilities for displaying entered data and for displaying current operational data, including nurse identification and/or number display 42, a unique patient identification name and/or number display 44, a drug name or other identification display 46, a dosage display 48, a rate display 50, a running time display 52, total volume of infusion display 54 and possibly other displays such as alarm display 53. For example, an alarm may be displayed upon detecting air in the line or occlusion limitations or other conditions, may be beneficially displayed or otherwise signaled to the operator. The monitoring circuitry 41 also provides the entered data and the current operating data to a wireless transmitter 45 for wireless transmission to an HIMS 60 (shown schematically as a remote computer terminal including wireless receiver unit 61, a CPU 57 and display 55 such as a CRT screen. A data input unit 59, such as a keyboard, a mouse, or another data entry device may also be connected to the HIMS 60.

For purposes of operating the pump according to the present invention, a power switch or power button 56 is provided on the control panel 22 and also a plurality of infusion data input controls 58, schematically represented as buttons 58, are provided for manually entering rate, entering volume to be delivered, for accessing a menu of drugs and options, and for toggling or otherwise selecting between various menu items, as well as for entering available menu items. These menu items will typically include available drug information, rates and dosage and other pump control information in order to effectuate programing of onboard pump control software or circuitry 43. Menu items may be selected using a toggle or other mechanism and may be appropriately entered into the pump control software or circuitry for operating the pumping mechanism.

With the understanding that any of a variety of possible types of IV pumps may be used in the present invention, the inventive wireless communication system according to one embodiment can include an IV pump 10 having pump operation circuitry 41 and circuitry 43 for monitoring preselected characteristics of pump operation. It will be understood from this disclosure that the operation circuitry and the monitoring circuitry may be separate electrically connected circuitry or software or integrally formed as unitary circuitry or software. The pump operational characteristics 15 such as parameters and states selected to be monitored may be those that are specifically indicative of IV administration of medication to a patient 20. A transmitter 45 is connected to the pump 10, as for example through the monitoring circuitry 41, for transmitting a wireless pump signal 49 representing the preselected pump operation characteristics . The wireless pump transmitter 45 communicates with a hospital information management system (HIMS) 60. The HIMS 60 includes a receiver 61 capable of receiving the pump signal 49 representing the pump operation characteristics and also includes a computer processor 57 capable of storing and displaying the pump operation characteristics on a display 55 represented by the wireless pump signal 49 received as through receiver antenna 63.

In another combination of elements depicted in FIG. 2 to demonstrate an alternative embodiment, an IV medication infusion pump 10 is provided for use with a hospital information management system 60 (HIMS), having a doctor's order 82 transmitter 83 capable of manually receiving an input doctor's order 82, as by a keyboard 85, for patient medication to be administered with an IV pump 10. The doctor's transmitter 83 is capable of wirelessly transmitting a wireless signal 87 representing the input doctor's order 82. The hospital wireless communications system 9, having the IV pump 10 with wireless transmitter 45 and a receiver 61 at the HIMS 60, is thus expanded, according to this alternative embodiment to receive a wireless signal 87 representing the doctor's order 82 for IV medication 17 for a patient 20. The doctor's order transmitter 83 provides a wireless signal representing the input doctor's order for patient medication that is to be administered intravenously, namely using the IV pump 10. In one such embodiment the doctor's order signal 87 is received at receiver 61 by the HIMS 60 for storage and/or for comparison to the actual operation characteristics as represented by the signal 49 transmitted from the IV pump 10. The storage and comparison may be carried out using an appropriate CPU 57. The pump 10 may also be provided with wireless signal receiver 51 to receive the doctor's order wireless signal 87 directly. Alternatively, the HIMS may also be provided with a transmitter 65 to provide to the IV pump 10, a HIMS wireless signal 67 that may include a retransmission of the doctor's order wireless signal 87, selected portions of the instructional content of the doctor's order 82, or other data or instructions such as instructions input at keyboard 59 or stored at CPU 57. The receiver at the IV pump 10 is capable of receiving such data or instructions for entry into the IV pump controls 43. At the pump data or instructions entry and pump activation will be according to appropriate safeguard, such as verification by the nurse or other health care professional responsible for the particular hospital patient. Other possible components of the system 9 might also be capable of communication with the HIMS using wireless signals.

In another combination of elements demonstrating yet another alternative embodiment, a pharmacy receiver 88 may also be provided that is capable of receiving a wireless signal representing the doctor's order for medication. The wireless signals 87 may be communicated directly between the doctor transmitter 83 and a pharmacy receiver 88, or between the doctor transmitter 83 and the IV pump 10. The pharmacy receiver may comprise a transceiver to communicate directly with the IV pump via wireless signal 91 or with the HIMS via wireless signal 89. The IV pump 10 may wirelessly communicate with the HIMS 60 and the HIMS 60 may wirelessly communicate with the IV pump, with the pharmacy 88, or with the doctor's transmitter 83. Alternatively, all of the individual components could wirelessly communicate with the HIMS 60 where the information could be re-transmitted to any of the other system components intend to receive the wireless signal representing selected information. In this alternative embodiment, the pharmacy receiver 88 includes apparatus 84, such as a computer terminal 84, for providing the order for patient medication in human readable form for the preparation of ordered patient medication for IV pump administration. The medication is provided by the pharmacist to a nurses' station according to the doctor's orders for proper administration to a patient receiving care from nurses who will be operating the IV pump. In this alternative embodiment and in addition to the wireless signal transmitter 45, the IV pump 10 also has a receiver 51 for receiving the wireless signal indicating the doctor's order. The signal indicating the doctor's order to the IV pump 10 may be a direct signal 87*i* from the doctor's order transmitter 83 or it may be a signal 91 from the pharmacy transmitter 88 or it may be a re-transmission signal 67 from the HIMS 60. In each case where a wireless signal transmitter and receiver is provided, there maybe separate transmitters and receivers electronically interconnected, or there may be a combination transmitter and receiver unit known as a transceiver.

Figure 3:
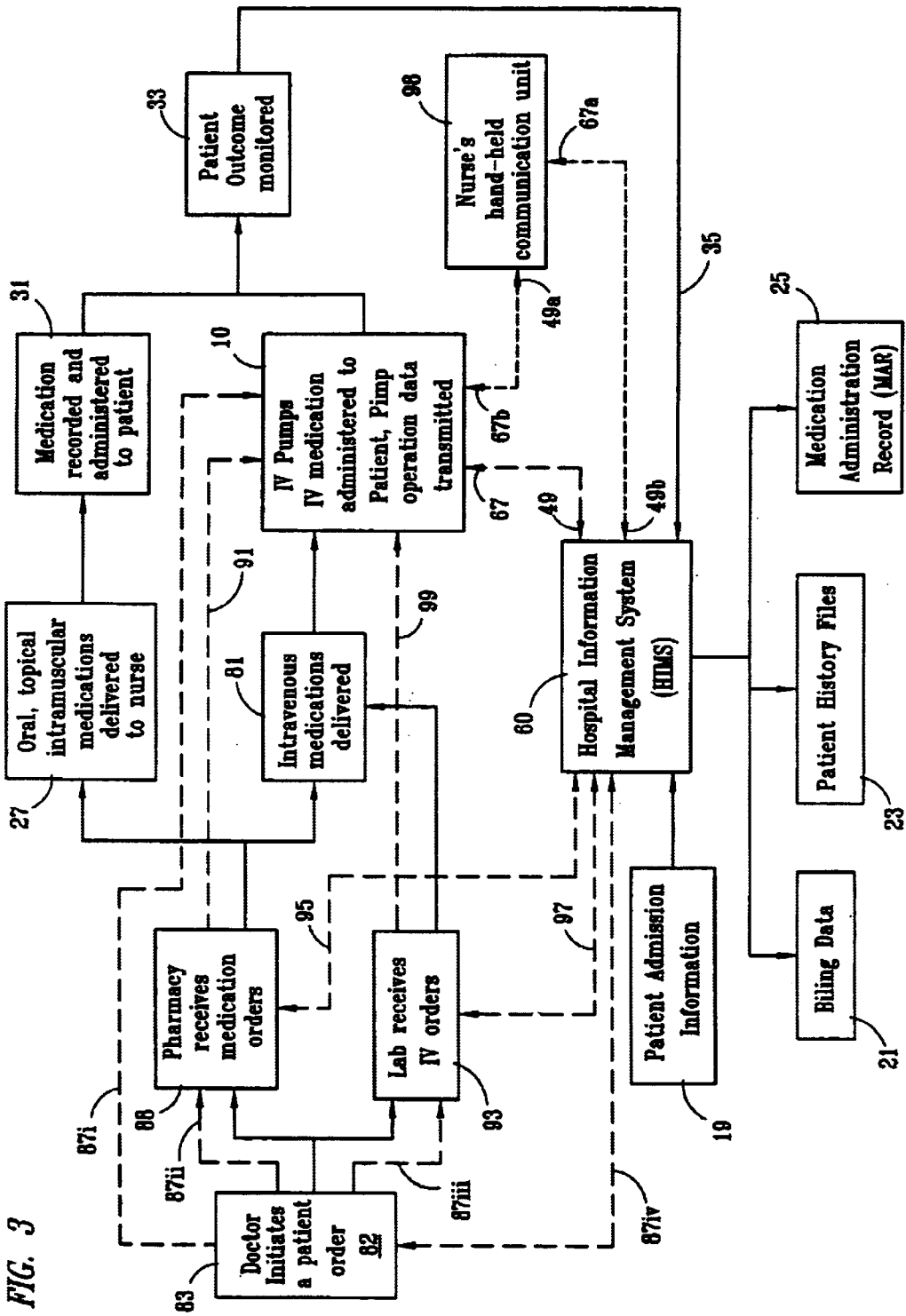
FIG. 3 is another schematic depiction of a wireless communication system from an IV pump to an HIMS and also depicting wireless communication among other elements of a hospital system including the IV pump and the HIMS.

Referring to the schematic flow diagram of FIG. 3, further combinations of inventive features may be understood. In this schematic the IV pump 10 for administering IV medication to a patient and for pump operation data transmission to a hospital information system HIMS 60, are depicted among other components in a flow diagram. Medication is ordered, prepared and delivered to a patient in a hospital or other institutional health care facility. The wireless communication signal 49 from the IV pump 10 to the HIMS 60 is depicted as dashed lines with the arrowhead directed toward the HIMS. The HIMS 60 might likewise communicate with the IV pump 10 along the dashed line as indicated by the arrowhead 67 pointing toward the IV pump. As will be discussed more fully below, the wireless communication between the IV pump 10 and the HIMS 60 might alternatively be in the form of a signal 49*a* from the IV pump 10 to a nurse's hand-held communication unit 98, and a retransmission signal 49*b* from the hand-held unit 98 to the HIMS 60, as depicted with dotted lines in FIG. 3. Similarly, the HIMS 60 may communicate to the IV pump with a transmission signal 67*a* to the nurse's hand-held communication unit 98 and the retransmission signal 67*b* from the hand-held communication unit 98 to the IV pump 10. It maybe understood that the doctor's transmitter and the nurses hand-held unit may be the same or similar type of wireless communication devices used for different purposes at different parts of the system by different professional healthcare givers.

To understand how the IV pump communication with HIMS may fit in the entire IV medication delivery process and system 9, we may look at the doctor's initiation of the patient order 82. This order may be communicated via wireless transmitter 83. A wireless signal from the doctor's transmitter 83 may be received directly by the IV pump 10 as indicated by dashed line 87i. Alternatively, the doctor's order may be wirelessly transmitted and received by the pharmacy transceiver 88, as indicated by dashed line signal 87ii. In the case where the doctor's order requires blood products or other laboratory prepared IV solutions, the doctor's order may be transmitted to and received by a laboratory receiver or transceiver 93 via wireless signal 87iii. Alternatively, the doctor's transmitter 83 may provide a signal 87iv to be received by the HIMS transceiver 61. The HIMS may be used to re-transmit the doctor's order with or without appropriate modifications such as additional instructional information to the pharmacy via wireless signal 95 or to the laboratory 93 via wireless signal 97. The pharmacy 88 or the lab 93 may be provided with a transceiver such that medication orders received in the pharmacy 88 or received in the lab 93, whether received from the HIMS or from the doctor's order transmitter 83 or otherwise, may be then appropriately prepared for administration to the intended and properly identified patient 20. The doctor's order, with additional instruction from the pharmacy as appropriate for a particular medication preparation or for a particular patient, may be transmitted via a wireless signal, wireless signal 91 in the case of the pharmacy and wireless signal 99 in the case of the lab, to the IV pump 10. The prepared medication or the prepared blood product or other laboratory IV solution container is then physically provided to the nurse's station for delivery to the pumping unit at the patient's hospital room, as indicated by the solid line and direction arrow head to block 81 in FIG. 3. The prepared IV medication container or prepared blood product container 12 is then appropriately attached to the IV pump 10. The IV pump 10 may receive a wireless signal indicating the appropriate instruction pumping characteristics for the IV fluid container that is connected to the IV pump 10 for the identified patient 20. Such infusion data and pumping characteristics will nevertheless need to be validated by the nurse in order to maintain the integrity of the system. For example, the nurse may enter the information from the IV fluid container identifying the medication, may also identify the patient, and may provide the nurse's identification consistent with authorization to administer medications to the patient. The pump operation data may be downloaded from the doctor's order, from the pharmacy instructions or from the HIMS 60. For purposes of central administration control, the doctor's order and/or the pharmacy instructions may be wirelessly received at the HIMS and such order and instructions may be checked and corroborated with patient information and/or medical information stored in the HIMS for purposes of confirming proper administration to the patient. In that embodiment, the nurse may activate wireless downloading of pump operation data from the HIMS 60 to IV pump 10, as, for example, by wireless signal 67.

It will be noted in FIG. 3 that the inventive wireless IV pump system works with and as a compliment to other health-care services provided to the patient and managed with a hospital information management system. For example, the patient admissions information 19 may be provided directly to the HIMS. Also, where the pharmacy prepares oral, topical or intramuscular medications, those medications may be delivered to a nurse's station as indicated by solid arrow to block 27 and the oral, topical or intramuscular medication may be recorded and administered to the patient as indicated by solid arrow to block 31. The patient outcome may be further monitored appropriately as with a patient's written chart 33 and that information may be conveyed to the HIMS, as indicated by arrow 35. In this manner, the HIMS 60 may receive information from any combination of various elements, or from all of the various elements of the patient health-care system 9. The information maybe appropriately used in providing billing data at block 21, providing a patient history file at block 23 and/or providing a medication administration record (MAR) at block 25.

In FIG. 3 a nurse's hand-held communication unit 98 is also shown in the phantom lines, for purposes of indicating yet another alternative embodiment of the system. Additional aspects of this alternative embodiment may also be understood, with reference also to FIG. 4. The nurse may use a hand-held communication unit 98 to manually enter information from a label on an IV container. The nurse may transmit the instructional data to the IV pump and upon confirming that the patient, medication and pumping data match, the nurse may initiate IV pumping. Alternatively a hand-held communication unit 98 specially adapted with bar code reading capabilities may be used to scan an IV container bar code information. Further alternatively, the nurse may receive a pharmacy medication instruction signal wirelessly and/or a doctor's order signal wirelessly by which the patient medication can be compared to the label on the physical IV container of fluid. As a further alternative, the nurse may enter an appropriate patient and IV medication identification into the hand-held communications unit 98 and this identification may be wirelessly transmitted to access the HIMS for receiving from the HIMS such information and instructions for IV pump administration of the identified IV medication to the identified patient. Those pump characteristics maybe transmitted to the hand-held unit via signal 67*a* and retransmitted to the IV pump from the hand-held communications unit via wireless signal 67*b*. Again upon confirming the information loaded into the IV pump, the nurse may activate pumping operations.

The hand-held communications unit 98 can similarly be used by the nurse to receive a wireless signal from the IV pump, indicating the IV pump operation characteristics at any point in time. The nurse may choose to poll any given IV pump as by using individual pump identification codes or addresses. Alternatively, the entire operation log for IV pump operation characteristics over a period of time might be uploaded to the handheld unit 98 on the command of the nurse. The pump operation characteristics, received by wireless signal 49*a*, can then be retransmitted to the HIMS as by a wireless signal 49*b*.

Figure 4:
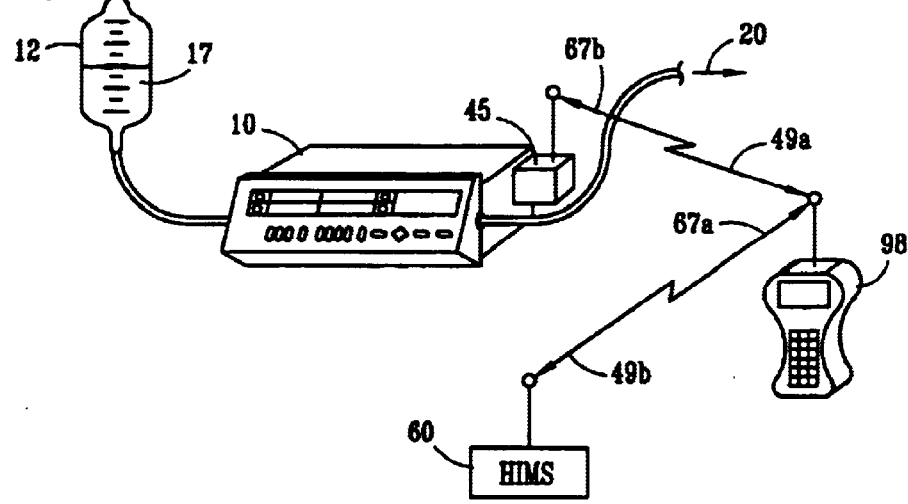
FIG. 4 is an alternative embodiment of the wireless communication system for IV pump and HIMS with an intermediary hand held transceiver.

This alternative embodiment may be more fully understood with reference to FIG. 4 in which only the nurse's hand-held communication unit 98, the HIMS 60 and the IV pump 10 are depicted as an alternative inventive subcombination of the invention. In this subcombination, the information from the IV pump is transmitted via wireless signal 49*a* and is received by the hand-held unit 98. The information may be displayed to the nurse and the nurse may retransmit the received information via signal 49*b* to the HIMS 60. Similarly, the nurse may wish to compare the current pump operation characteristics 15, represented and received as wireless signal 49*a*, with the desired pump operation characteristics received from the HIMS. The nurse may do this by way of activating and receiving a wireless signal 67*a* from the HIMS to the hand-held unit 98. Thus in certain appropriate situations, the HIMS operational instructions represented by signal 67*a* may be transmitted by the hand-held unit activated by the nurse as a wireless signal 67*b* to the IV pump 10. Where a plurality of IV pumps 10, 10*b*, 10*c*, 10*d*, and 10*z* may be present pump identification codes may be used to access only the desired pump. The IV pump id would likely be readable from the pump itself so that there is no doubt that the proper pump at the identified patient's bedside is being accessed and/or programmed for infusion operation by the nurse.

Figure 5:
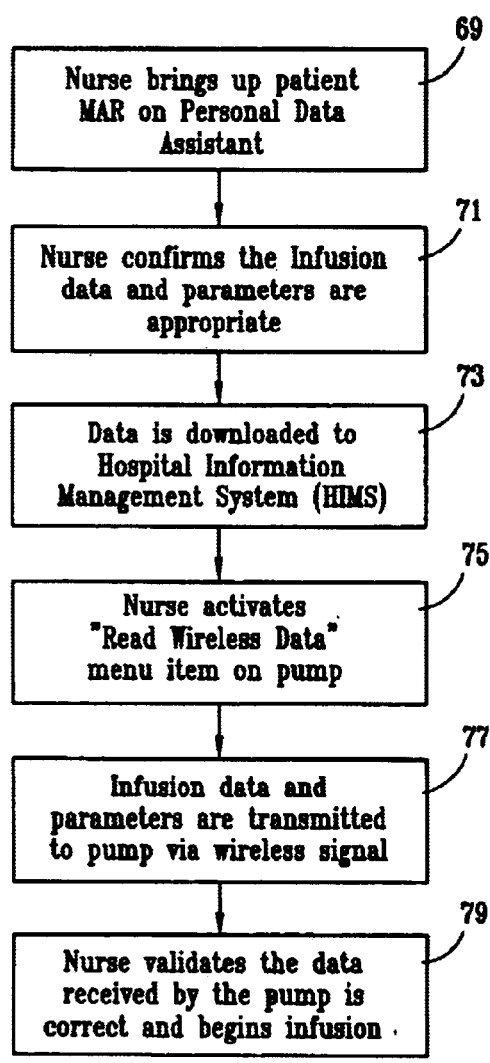
FIG. 5 is a schematic flow diagram demonstrating use of a wireless communication system at the pump according to one aspect of the present hospital system and IV pump wireless communication system.

FIG. 5 schematically depicts an enhanced security operating sequence for operating an IV pump with wireless signal transmitter 10 as well as the nurse's hand-held wireless signal transmitter 98. In this method, a nurse brings up a patient's medication administration record (MAR) on the hand-held unit 98 at step 69. The nurse then confirms that the infusion data and IV pump operating characteristics are appropriate for the MAR information for the identified patient at step 71. Where the characteristics are appropriate, data is communicated to the HIMS at step 73 and the nurse activates the read-wireless data menu on the IV pump at step 75. With the read-wireless data menu item activated, the infusion data and characteristics are transmitted to the pump via wireless signal, according to step 77 in FIG. 5. With the infusion pump characteristics thus entered wirelessly into the infusion pump, the nurse may validate that the data received by the IV pump is correct. This may be done by observing the pump display 40. Upon validating the accuracy of the entry, the beginning of infusion may be authorized at step 79.

In each embodiment the IV pump has at least one transmitter for transmitting at least one wireless signal to the HIMS. The transmitter is operatively connected to certain pump operation circuitry for monitoring preselected pump operations and for transmitting a wireless signal representing such preselected pump operational characteristics indicative of IV administration of the patient medication to a patient. The HIMS is provided with a wireless signal receiver capable of receiving the signals from the IV pump transmitter.

While the IV pump 10 is operating, the operational characteristics 15 of the pump may be monitored with appropriately connected circuitry, software or a combination of circuitry and software all referred to herein as circuitry 41. The monitoring maybe done continuously, at regular intervals, at predetermined irregular intervals, or upon the occurrence of predetermined events, or upon the occurrence of any event that changes the state of the pump. By way of example, such state change events could include starting or stopping, changing of infusion rate, activation of an alarm, or approaching a predetermined time in advance of an anticipated event. The information regarding the pump operation is transmitted by the wireless pump transmitter to the HIMS wireless signal receiver. Again information acceptance, storage, comparison and/or etc., may be performed by HIMS programs or circuitry. Information wirelessly transmitted to the HIMS by the pump transmitter may include other information such as medication name, patient ID, and nurse ID when available in addition to operational characteristics . Also, pump alarm conditions, malfunction conditions, and maintenance conditions may also be transmitted.

End of infusion warnings may be advantageously signaled according to one alternative inventive aspect of the invention. For certain types of medication such as antibiotics, causative medications, vasoactive medications and antiblood clotting medications, the end of infusion warnings will desirably be programmed or programmable to occur with sufficient lead time for the HIMS to "notify" the pharmacist to prepare the next medical solution and have it delivered to the patient's IV pump before the current bag is completely emptied. Other information such as administrative information including for example specific pump ID, pump location and hours of operation, and any maintenance reports may also be transmitted to the HIMS via wireless signal transmission. For example spaced apart HIMS receiver nodes with known locations throughout the hospital or health care facility may receive signals from the plurality of IV pumps and by pump ID codes and signal strength and/or signal direction means the location of the pumps within the facility may be determined.

In one embodiment the pump may also be capable of downloading the pump operation log (Op log). For example, the Op log may be transmitted to the HIMS at each nurse shift change, at regular timed intervals, or upon receipt of a HIMS inquiry signal transmitted to the IV pump.

Wireless communication between the doctor's order transmitter 83, the pharmacy transmitter 88, and the IV pump transmitter 45 or between any combination or from all of the components may also facilitate medical administration to a patient in a hospital or other institution or healthcare facility.

A computer processor 57 of the HIMS 60 may be provided that is capable of storing the information represented by the received signals. The HIMS 60 may also include software or circuitry that is capable of comparing doctor's order for patient medication with pharmacy instructions and/or capable of comparing the doctor's order or the pharmacy instructions with the wirelessly transmitted IV pump characteristics indicative of the actual delivery of medication to the patient. The HIMS may be programmed for comparing the doctor's order to the actual pump operation delivery characteristics. The comparison may for example, confirm successful doctor ordered delivery or it might determine that delivery was not completed as instructed. According to yet another alternative configuration of the invention, the HIMS will be able to display, in human readable form, the order, the pump operation characteristics and the results of the comparison indicative of successful completion of administration of this ordered medication to the patient or otherwise. The HIMS can be useful to communicate the information to billing at 21, to patient history files at 23, and to a medication administration record (MAR) at 25 for monitoring safe and secure records of medications, especially controlled substances. In yet other possible combinations with the present invention the type of blood product to be infused might be compared to patient blood type information in the HIMS or patient allergies to medications to be infused might be compared to HIMS records for the patient.

In yet another embodiment the pharmacist's instructions in bar code format may be scanned into the IV pump from a bar coded IV bag, bottle, syringe or other container labeled by the pharmacist and scanned with a bar code scanner connected with the IV pump. The bar code scanning capability may be selectively activated by an authorized nurse or other authorized healthcare professional. Upon activation, the nurse is prompted to scan a nurse's ID, which ID includes a special authorized user code. If the authorization code is present, then the pump prompts the nurse to scan in the patient's ID. When the patient ID is properly scanned, then the nurse is prompted to scan information from the pharmaceutical fluid container, whether a bag, a bottle, a syringe or another container. Upon reading information from the label of the container of medicinal fluid, pump control software displays an appropriate display of the name of the drug identified by the bar code label. The software may further capture the drug name, the concentration, concentration volume, volume to be delivered and infusion rate, if not calculated. All of these operation characteristics might be selected for wireless transmission to the HIMS. If all of the required infusion information is validated by the nurse, then the infusion maybe initiated according to the accurately scanned infusion information such as the volume to be delivered and infusion rate that is read directly from the infusion information bar code label on the fluid container and into a control program of the infusion pump. If any of the required information cannot be accurately validated by the nurse, then the scan mode is exited and the nurse must manually input the required data and infusion rates into the pump software control program using control panel buttons, toggles and displays. Any portion or all of the pump operation activity may be transmitted wirelessly to the HIMS or it may be stored in the a pump operation log that may subsequently be transmitted via wireless signal to the HIMS. Any or all of this information might be selected for transmission to the HIMS for storage or for comparison to the doctor's order. If there is a mismatch, an alarm or warning might be issued to the appropriate personnel or directly to the IV pump.

According to the alternative embodiment shown in phantom lines at 62 and 64 in FIG. 2, the pump housing 11 also carries an operably connected bar code scanner 62, having a scanner window 64 depicted on the side of the pumping housing 11, it being understood that the scanner window 64 might also be in another position or otherwise directed for usefulness of the pump, however in the embodiment depicted where a plurality of pumps 10 might be stacked one on top of the other, attached through pole clamps 28 to a pole 29, it is preferred to provide the scanning window 64 facing toward a side or toward the front. The side being advantageous as a position for the bar code scanning window because of the effective use of the front panel 22 for display and manual programming.

The bar code scanner 62 is useful with a container 12, having a pharmacist prepare therapeutic fluids 70 therein. The container is provided with a bar code label 66 and preferably also a human readable printed infusion data label 68 corresponding to the bar code information on bar code label 66. The operator may activate the scanning mode by using menu and cursor keys to activate a menu item. The pump will prompt the user to provide certain required security information, such as including a scan of a nurse's ID badge or card. A nurse's ID badge will preferably have a unique identification code number and also an appropriate authorization code. Only with the authorization code and the nurse's ID can the scanning mode be continued. Subsequent to scanning in the nurse's ID, a unique patient ID must be scanned, as from a patient wrist band or a patient ID card, having a bar code to uniquely identify the patient by name and/or by patient number. After the nurse's ID and the patient's ID are appropriately scanned and confirmed, as by using the "E" or "enter" button 100 or other appropriate confirmation, then the bar code label 66 of the medication container 12 can also be scanned. The bar code label on the medication container 12 is prepared by a pharmacist that also prepares the medication 17. The infusion information may include the unique patient identification field 72, the drug name or identification 74, a dosage 76, a rate 78 and other infusion information 80, as may be appropriate. For purposes of further confirmation, all the requisite information may also be printed in a human readable label 68 corresponding to the bar code fields that are scanned for convenience and accuracy.

Figure 6A:
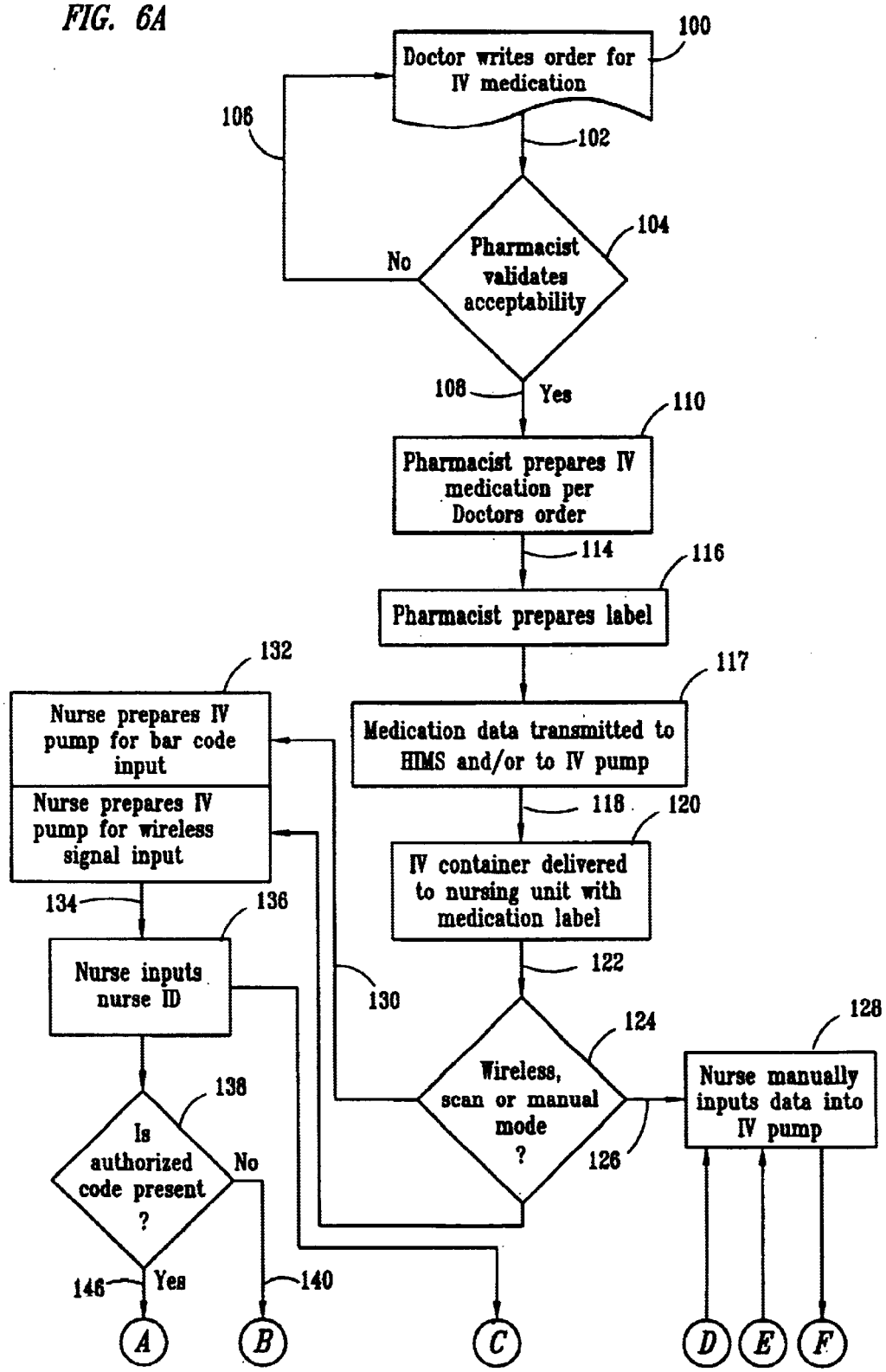
FIG. 6 (including FIG. 6A continuing on FIG. 6B) is a schematic flow diagram further depicting a wireless communication IV pump and HIMS system further including a bar code reader for entry of IV medication pumping information into the IV pump according to an alternative embodiment incorporating certain aspects of the invention.
Figure 6B:
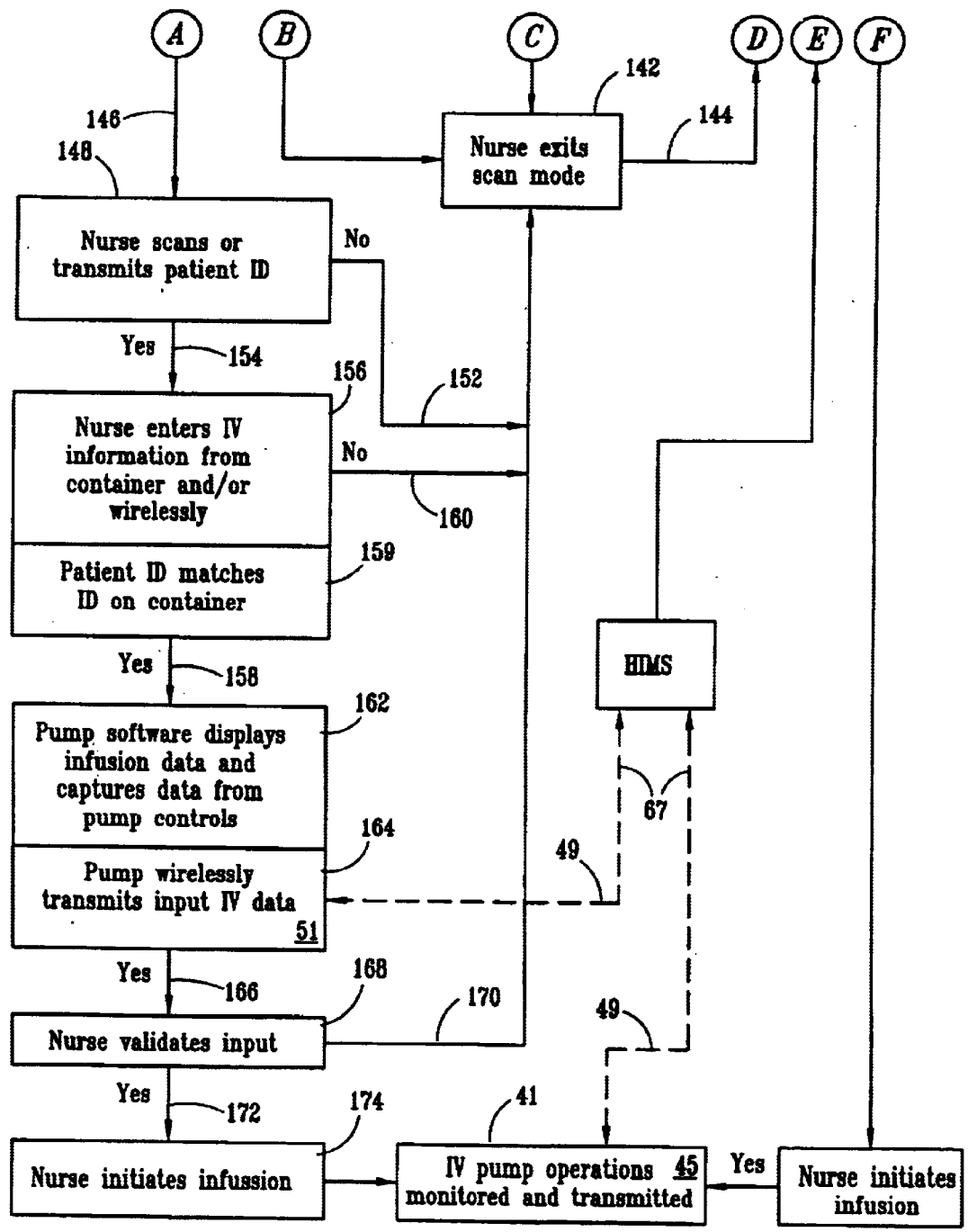

FIG. 6 is a schematic flow diagram of the operation of one alternative embodiment of a wireless signal transmitter pump in a system for improved accuracy and security using wireless signal transmission to a HIMS. In this flow diagram, the initial step is for the doctor to make an order for medication as at step 100. The order for the medication goes to a qualified pharmacist and, in particular, a pharmacist who prepares medications for the institution at which the infusion will be administered as indicated by arrow 102. In step 104 the pharmacist receives the order and validates the acceptability of the medication ordered for a particular patient. If, for any of a number of reasons, the pharmacist believes that the medication is not acceptably written by the doctor, then the pharmacist sends the order back to the doctor, as indicated by arrow 106, so that the order may be rewritten to be acceptable to the pharmacist. In the event that the order is acceptable, then the pharmacist moves to the next step, as indicated by arrow 108, to step 110 for the preparation of the medication according to the doctor's written order. Immediately upon preparing the medication per the doctor's order, the pharmacist then moves to the next step, as indicated by process arrow 112, to step 114, where the pharmacist prepares a label 116 for the medication. With additional information available to the pharmacist through the healthcare facility's admission records as stored in the HIMS, the prepared labels may also include the patient's name, the patient's identification number, as assigned in the admissions procedure. The label includes the drug name, according to the preparation made by the pharmacist, the concentration, the concentration volume, the volume to be delivered and the infusion rate, if not calculated. The patient's height and weight may also be provided or other appropriate infusion data, if it is applicable to the therapy anticipated by the infusion. Referring again to FIG. 2, the pharmacist may be provided with a wireless transmitter 88 connected to an input 91 and keyboard 93 terminal by which the information for the medication is entered into the terminal 91 and transmitted via transmitter 88 to the HIMS 60 receiver 61. The pharmacist may prepare human readable labels and may also be provided with bar code specifications, to provide labels bar code readable by the infusion pump.

The pharmacist then releases the container 12 of the medication 70 and transmits the medication data to the HIMS. The medication itself is then delivered at 118 to a nursing unit appropriately assigned to the identified patient 20, as indicated at step 120. The assigned nurse or other authorized healthcare professional then carries the medication container 12 to the patient's room, bedside and infusion pump where the medication data including pump operating instructions are input into the pump control circuitry, as indicated by arrow 122. The nurse or other authorized healthcare professional might scan the infusion information into the pump where a bar code scanner is available, or might input the infusion data manually, or might activate wirelessly transmission of IV information to the IV pump as indicated by decision box 124. The pharmacist may wirelessly transmit the medical information to the HIMS. In the embodiment where the IV pump is also provided with a wireless receiver (or a transceiver), the data may be transmitted to the IV pump directly from the doctor, the pharmacist, the HIMS or from the nurse's handheld communication unit. This provides the healthcare institution with the options to instruct authorized personnel to input the data manually, to provide bar code labels to allow the data to be scanned in for improved administration capabilities provided by the bar code scanner or to download the medication instructions from the HIMS. In any event, the nurse validates the input data as it is displayed at the pump before initiating pumping.

The healthcare institution may phase in the use of the wireless pump communication capabilities, or alternatively, may determine appropriate criteria for internal purposes for wireless transmission of certain types of infusion medications, scanning other types of data and/or manually inputting other data. The infusion pump may be provided with recording capabilities such as computer chip memory, so that appropriate infusion data is recorded in an operation log (Op log) reviewable for administration purposes, for quality control purposes and, importantly, for purposes of the physician's review to determine appropriate continued or future treatment or medications for the patient. The recorded pump information may be wirelessly transmitted to HIMS. If the manual input mode is selected as indicated by arrow 126, then the nurse enters the infusion data from the control panel 22, as indicated by action block 128. When the automatic infusion data entry is determined to be appropriate, as indicated by arrow 130, the nurse then prepares the pump for input data or for wireless transmission input, as indicated at step 132.

Preparation of the pump for bar code input or wireless input includes not only turning the pump on, as with a power button 56, but also setting the pump for the automatic bar code scanning mode or wireless receiving mode. This may be done from a menu or otherwise depending upon the pump controls. When the pump is determined to be in the scan mode, as indicated by arrow 134, the nurse will be prompted to scan in a nurse's ID with a bar code on an ID tag (also made with a compatible bar code labeling system for use with the bar code module used in the device). Advantageously, all authorized healthcare professionals employed by the healthcare facility with qualifications for establishing an infusion to a patient, will be provided with an identification tag, badge, card or other coded identifier having a specialized authorization code. If the authorization code is present, the automatic bar code scanner may be initialized for establishing infusion data for a patient, as indicated by block 138. If the authorization code is not present or if the nurse does not scan in an appropriate ID, then the automatic system requires the nurse to exit the scan mode, as indicated by arrow 140. If infusion continues to be desired after the scan mode is exited, then the nurse decides, at block 142, whether to move to the manual input mode, as indicated by arrow 144, thus moving the nurse back to block 128 for manually inputting data into the pump, or to start over with the scan mode initialization.

If the nurse's ID is properly entered at 136 and if the authorization code is present in the entered ID, as indicated by 138, then the control software allows the nurse to proceed, as indicated by arrow 146. The nurse is prompted to scan in the patient's ID, at step 148. The patient's ID may appropriately be established with a wristband having a bar code for the patient's ID set forth thereon, or alternatively, where the patient's care limits the availability of using the wrist band for scanning purposes, the patient's ID may be on a patient card, a patient badge, or on the patient's chart, or other bedside available bar code so that proper patient identification is securely established. According to a preferred security check, a patient ID must be scanned in order for the automatic bar code scanning mode to continue. If the patient's ID is not scanned, as indicated by arrow 152, the nurse is then returned to decide whether to manually input the data into the pump, as at decision block 142 and manual input block 128, as described above.

If the patient ID is scanned, as indicated with arrow 154, the nurse will be prompted to either scan in the infusion information from the container, as set forth in action block 156, or receive a wireless signal from the HIMS. The scanning of the information from the container would involve scanning the bag, bottle, syringe or other medication container past the bar code scanner window 64 with an appropriate confirmation that the scanning was completed, as by an audible sound signal, a visual signal or both. If the container information is readably scanned from the container, then the process would move forward, as indicated by arrow 158. If not, then, as indicated by return arrow 160, the nurse would be again returned to decision block 142 and manual input action block 128.

In the event that all the infusion data can be appropriately validated by the nurse or healthcare professional at the pump, as set forth in step 168. If the nurse cannot validate the input or any aspect of the input, then the system returns the nurse, as indicated by line 170, to exit the scan mode at 142 and to either move to the manual input 128 or otherwise correct the situation. Assuming the nurse can validate the accuracy of all the required input data as automatically downloaded, then the nurse initiates the infusion, as indicated by arrow 172 and action step 174.

A wireless communication system from an IV medication infusion pump to a hospital information management system (HIMS) is provided including a medication order transmitter capable of receiving input of a doctor's order for patient medication to be administered with an IV pump. The IV pump is uniquely capable of wireless transmission of a first signal representing the input doctor's order for patient medication that is to be administered intravenously, namely using the IV pump. A pharmacist receiver is provided that is capable of receiving the first signal representing the doctor's order for medication and having circuitry for providing the order for patient medication in human readable form for the preparation of ordered patient medication for IV pump administration. The medication according to the doctor's orders as may be enhanced or supplemented by the pharmacist for proper administration to the patient are provided to the IV pump. The IV pump having a receiver for receiving the first signal indicating the doctors order, also has a transmitter for transmitting a wireless signal that might be designated a second signal for discussion purposes. The transmitter is operatively connected to certain pump operation circuitry for monitoring preselected pump operations and for transmitting such a second wireless signal representing preselected pump operation characteristics indicative of IV administration of the patient medication to a patient. A hospital information management system is provided with a signal receiver capable of receiving the first and second signals. A computer component of the HIMS that is capable of storing the information represented by the received signals is also provided with software or circuitry that is capable of comparing doctor's order for patient medication with the IV pump characteristics indicative of delivery of medication to the patient. The HIMS is thus programmed for comparing the doctor's order to the actual pump operation delivery characteristics . The comparison may for example, confirm successful doctor ordered delivery or it might determine that delivery was not completed as instructed. The HIMS will be able to display the order, the pump operation characteristics and the results of the comparison indicative of successful completion of administration of said ordered medication to said patient or otherwise.

In one embodiment the pumping instructions in bar code format may be scanned into the IV pump from a bar coded IV bag, bottle, syringe or other container labeled by the pharmacist and scanned with a bar code scanner connected with the IV pump.

Thus, what has been disclosed is a system and medical infusion pump with bar code reading and wireless communication capabilities, to provide pump operation characteristics to an HIMS in a hospital or other healthcare institution or facility. The medical infusion pump with the bar code reader, the wireless signal transmitter and the HIMS capable of receiving, storing and displaying information derived from the operation characteristics also forms a part of a patient care system. The patient care system provides for an authorized pharmacist to prepare and label infusion fluids including medicines, drugs, and other pharmacological infusion products to be infused to patients upon doctor's orders. The labeling information may include patient ID, patient height, patient weight, drug information and drug administration dosage and rate information. The patient's doctor orders medicines directly from the pharmacist and the pharmacist prepares the infusion fluid and labels the container from which the fluid will be infused to the patient. The pump is provided with operation parameter monitoring circuitry connected to a wireless transmitter by which the characteristics are transmitted to the HIMS. The authorized healthcare professional such as the nurse must scan in their own personal ID and an authorization code to indicate their authorization to administer medicines to the patient. The authorized user confirms the accuracy of the pump operational instructions prior to administration of the medicine to the patient. Thus only an authorized healthcare giver such as an identified nurse is permitted to activate the pump for operating according to information loaded into the pump control circuitry or software after confirming that the patient information as well as the drug administration information as it is displayed at the pump. In any event whether the IV pump is instructed to operate wirelessly, with a bar code scanner, manually or otherwise, the wireless transmission of IV pump operation characteristics to the HIMS is advantageous to the patient and to the hospital for increasing the security, efficiency and effectiveness of health care provided to patients requiring IV medications and treatments.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. An IV medication infusion pump for use with a hospital information management system (HIMS), said IV pump comprising:
   (a) pump operation circuitry coupled with said infusion pump for monitoring preselected characteristics of current infusion pumping operation;
   (b) a wireless signal transmitter connected to said pump operation circuitry for transmitting at least one wireless signal representing said preselected current pumping operation characteristics; and
   (c) a receiver capable of receiving said at least one wireless signal representing said current pumping operation characteristics, said receiver connected to said hospital management system (HIMS) for receiving said current pumping operation characteristics represented by said at least one wireless signal from said IV pump.

2. The IV pump of claim 1 wherein:
   (a) said operation circuitry comprises circuitry monitoring a plurality of current pumping operation characteristics selected from among rate of pumping, pumping pressure, start time, time of pumping, volume of pumping, dosage, size of tubing, speed of pumping motor, door closed, manual programing mode, automatic programing mode, start-up testing, dosage of infusion and bolus of infusion; and
   (b) said at least one wireless signal comprises one or more wireless signals indicative of said plurality of current pumping operation characteristics of said IV pump.

3. The IV pump of claim 1 wherein:
   (a) said operation circuitry comprises input drug identification circuitry; and
   (b) said at least one wireless signal comprises a signal indicative of said drug identification input into said IV pump.

4. The IV pump of claim 1 wherein:
   (a) said operation circuitry comprises input patient identification circuitry; and
   (b) said at least one wireless signal comprises a signal indicative of said patient identification input into said IV pump.

5. The IV pump of claim 1 wherein:
   (a) said operation circuitry comprises input nurse identification circuitry; and
   (b) said at least one wireless signal comprises a signal indicative of said nurse identification input into said IV pump.

6. The IV pump of claim 1 wherein:
   (a) said operation circuitry comprises alarm condition detection circuitry; and
   (b) said at least one wireless signal comprises a signal indicative of said alarm condition of said IV pump.

7. The IV pump of claim 1 wherein:
   (a) said pump alarm condition detection circuitry further comprises circuitry to detect at least one pump alarm condition selected from among conditions of an invalid operator ID, an invalid patient ID, a door open condition, a high pressure condition, a flow blocked condition, an air in the line condition, a low voltage condition, a pump malfunction condition, and a pump stopped condition; and
   (b) said at least one wireless signal comprises a signal indicative of said at least one selected alarm condition of said IV pump.

8. The IV pump of claim 1 wherein:
   (a) said operation circuitry comprises time of infusion monitoring circuitry; and
   (b) said at least one wireless signal comprises a signal indicative of said time of infusion of said IV pump.

9. The IV pump of claim 1 wherein:
   (a) said operation circuitry comprises end of infusion warning circuitry; and
   (b) said at least one wireless signal comprises a signal indicative of said end of infusion warning of said IV pump.

10. The IV pump of claim 1 wherein:
    (a) said operation circuitry comprises advanced end of infusion warning circuitry; and
    (b) said at least one wireless signal comprises a signal indicative of said advanced end of infusion warning of said IV pump.

11. The IV pump of claim 1 wherein:
    (a) said operation circuitry comprises advanced end of infusion warning circuitry programable for providing a warning at a selected time in advance of said end of infusion; and
    (b) said at least one wireless signal comprises a signal indicative of said end of infusion warning of said IV pump transmitted said selected time in advance of the end of infusion.

12. The IV pump of claim 1 wherein:
    (a) said operation circuitry comprises pump operation log circuitry; and
    (b) said at least one wireless signal comprises a signal for downloading said operational log of said IV pump to said HIMS.

13. The IV pump of claim 1 wherein:
    (a) said receiver capable of receiving said at least one wireless signal from said IV pump comprises a plurality of receiving nodes positioned at predetermined locations throughout said healthcare institution for receiving said at least one wireless signal from an IV pump located within a predetermined short range of said node location;
    (b) said pump operation circuitry further comprises an individual IV pump identification signal unique to each pump in the health care institution; and
    (c) said at least one wireless signal comprises a signal indicative of said individual identification of said IV pump.

14. The IV pump of claim 13 further comprising node location detection circuitry connected to said HIMS for detecting the location of the node receiving a wireless signal from an individually identified IV pump so that the location of said IV pump within said health care institution can be determined at by said HIMS.

15. The IV pump of claim 1 wherein:
    (a) said wireless signal transmitter connected to said pump operation circuitry comprise a transceiver for both transmitting at least one wireless signal representing said preselected pumping operation characteristics and for receiving input signals from said HIMS; and
    (b) said receiver connected to said hospital management system (HIMS) comprises a transceiver capable of both receiving said at least one wireless signal representing said pumping operation characteristics and transmitting at least one input signal for providing at least one pumping operation parameter to said IV pump operation circuitry.

16. A wireless communication system from an IV medication infusion pump to a hospital information management system (HIMS) comprising:

(a) pump operation circuitry coupled with said IV medication infusion pump for monitoring preselected characteristics of current infusion pumping operation;

(b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;

(c) a wireless signal pump transmitter connected to said pump operation circuitry for transmitting at least one wireless signal representing said preselected monitored current pumping operation characteristics;

(d) an HIMS receiver capable of receiving said at least one wireless signal representing said pumping operation characteristics, said receiver connected to said hospital management system (HIMS) for receiving said current pumping operation characteristics represented by said at least one wireless signal from said IV pump, said HIMS receiver further capable of receiving said signal representing said doctor's order; and (e) wherein said HIMS further comprises programing for receiving, storing and comparing said pump signal with said signal representing said doctor's order to determine whether said medication is delivered to said patient by operation of said pump according to said doctor's order.

17. A wireless communication system from an IV medication infusion pump to a hospital information management system (HIMS) as in claim 16 further comprising:

(a) a pharmacy receiver for receiving said doctor's order signal representing said doctor's order, said pharmacy receiver operatively connected to a program and a display to provide human readable information sufficient for a pharmacist to prepare the ordered medication;

(b) a pharmacy transmitter for sending a delivery signal indicating that an IV medication has been delivered to a nurses station and representing that the IV medication is to be administered to a patient according to said doctor's order; and (c) wherein said HIMS further comprises programing for storing said delivery signal and for comparing said delivery signal to said order signal and/or to said pump operation characteristics signal to facilitate monitoring of the timely delivery of the IV medication to the patient according to the doctor's order.

18. A wireless communication system from an IV medication infusion pump to a hospital information management system (HIMS) as in claim 16 further comprising:

(a) laboratory receiver for receiving said order signal when a blood product IV is ordered for the patient; and (b) a laboratory signal transmitter for signaling to said HIMS the delivery of a blood product IV for administration to a patent and including information related to the time sensitivity of the blood product; and (c) wherein said HIMS further comprises programing for comparing said laboratory signal to said pump parameter signal so that actual timely delivery of said blood product represented by said laboratory signal can be monitored and the results of the comparison can be displayed.

19. A wireless communication system from an IV medication infusion pump to a hospital information management system (HIMS) as in claim 16 wherein:

(a) said transmitter connected to said pump comprises a transceiver for receiving signals corresponding to pumping operation characteristics according to said doctor's order for medication to a patient; and (b) said HIMS receiver comprises a transceiver for receiving said doctor's order and for transmitting another signal representing pumping operation characteristics a corresponding to said doctor's ordered medication for a patient.

20. A wireless communication system from an IV medication infusion pump to a hospital information management system (HIMS) as in claim 16 further comprising:

(a) a nurses station transmitter having an input for entry of information on IV medication received at a nurses station and for transmitting a medicine received signal representing the IV medications received for a patient upon receiving any ordered medication; and (b) wherein said HIMS further comprises programing for receiving and storing said IV medication received signal and for comparing said medication received signal with at least one of said order signal and said pumping characteristic signal to facilitate monitoring of preparation, delivery and administration of said IV medication and for providing the results.

21. A wireless communication system from an IV medication infusion pump to a hospital information management system (HIMS) comprising:

(a) a medication order transmitter capable of receiving input of a doctor's order for patient medication to be administered with an IV pump and capable of wireless transmission of a first signal representing the input order for said patient medication for IV administration;

(b) an IV pump having pump operation circuitry for monitoring preselected characteristics of pump operation and a transmitter connected to said pump operation circuitry for transmitting a second wireless signal representing said preselected pump operation characteristics indicative of IV administration of medication to a patient;

(c) a receiver for receiving said first signal and for providing said order for patient medication in human readable form for the preparation of said ordered patient medication for IV pump administration; and (d) a hospital information system including a receiver capable of receiving said first and said second signals and a computer processor capable of storing said information represented by said signals, capable of comparing said doctor's order for patient medication to said IV pump delivery of medication to a patient and for comparing said order to said delivery characteristics to determine whether medication delivery was as ordered by the doctor and for displaying said order and said pump operation characteristics and the results of the comparison thereof.

\* \* \* \* \*

(12) EX PARTE REEXAMINATION CERTIFICATE (7708th)
United States Patent
White et al.

(10) Number: US 6,790,198 C1
(45) Certificate Issued: Aug. 31, 2010

(54) PATIENT MEDICATION IV DELIVERY PUMP WITH WIRELESS COMMUNICATION TO A HOSPITAL INFORMATION MANAGEMENT SYSTEM

(75) Inventors: Gale White, Fort Worth, TX (US); Roger Hill, Richardson, TX (US); Michael J. Zakrewski, Carrollton, TX (US); Ruth Kummerlen, Frisco, TX (US); Martyn Stuart Abbott, Dallas, TX (US); Robert C. Brooks, Mabank, TX (US)

(73) Assignee: B. Braun Medical, Inc., Carrollton, TX (US)

Reexamination Request:
No. 90/009,503, Jun. 22, 2009

Reexamination Certificate for:
Patent No.: 6,790,198
Issued: Sep. 14, 2004
Appl. No.: 09/702,310
Filed: Oct. 31, 2000

Related U.S. Application Data

(63) Continuation-in-part of application No. 09/452,488, filed on Dec. 1, 1999, now Pat. No. 6,519,569.

(51) Int. Cl.
*A61M 1/00* (2006.01)

(52) U.S. Cl. .............................. 604/151; 604/67; 705/3; 700/237

(58) Field of Classification Search .................... None
See application file for complete search history.

(56) References Cited

U.S. PATENT DOCUMENTS

| | | |
|---|---|---|
| 3,780,907 A | 12/1973 | Colburn et al. |
| 3,826,900 A | 7/1974 | Moellering |
| 3,831,006 A | 8/1974 | Chaffin, III et al. |
| 3,848,112 A | 11/1974 | Weichselbaum et al. |
| 3,898,984 A | 8/1975 | Mandel |
| 3,917,045 A | 11/1975 | Williams et al. |
| 3,921,196 A | 11/1975 | Patterson |
| 4,121,574 A | 10/1978 | Lester |
| 4,473,884 A | 9/1984 | Behl |
| 4,491,725 A | 1/1985 | Pritchard |
| 4,523,087 A | 6/1985 | Benton |
| 4,636,950 A | 1/1987 | Caswell et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,767,917 A | 8/1988 | Ushikubo |
| 4,810,243 A | 3/1989 | Howson |

(Continued)

FOREIGN PATENT DOCUMENTS

WO     99/10029     3/1999

OTHER PUBLICATIONS

IMED Corp, IMED® Status™ Infusion Management System, IMED Leadership Through Innovation, San Diego, California.

*Primary Examiner*—Beverly M. Flanagan

(57) ABSTRACT

A wireless communication system from an IV medication infusion pump to a hospital information management system (HIMS) is disclosed. The system includes an IV pump having pump operation circuitry for monitoring preselected characteristics of pump operation indicative of IV administration of medication to a patient. A transmitter is connected to the pump operation circuitry for transmitting a wireless pump signal representing the preselected pump operation characteristics. The wireless pump transmitter communicates with a hospital information management system (HIMS). The HIMS includes a receiver capable of receiving the pump signal representing the pump operation characteristics and also includes a computer capable of storing and displaying the pump operation characteristics represented by the received wireless pump signal.

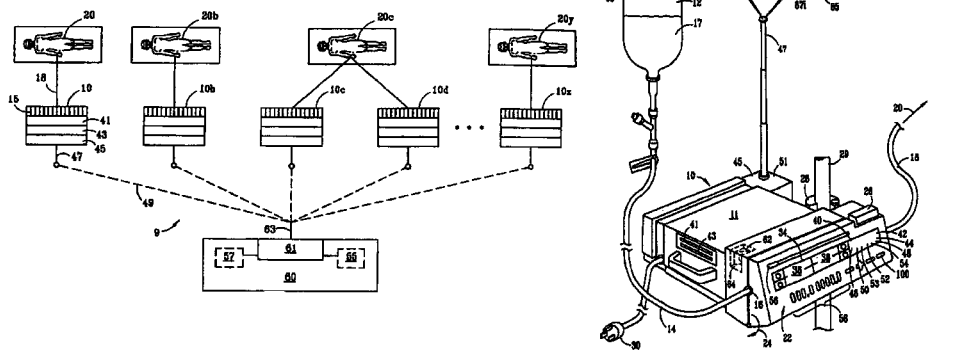

U.S. PATENT DOCUMENTS

| | | |
|---|---|---|
| 4,828,545 A | 5/1989 | Epstein et al. |
| 4,839,806 A | 6/1989 | Goldfischer et al. |
| 4,857,716 A | 8/1989 | Gombrich et al. |
| 4,893,270 A | 1/1990 | Beck et al. |
| 4,953,745 A | 9/1990 | Rowlett, Jr. |
| 5,036,852 A | 8/1991 | Leishman |
| 5,041,086 A | 8/1991 | Koenig et al. |
| 5,072,383 A | 12/1991 | Brimm et al. |
| 5,078,683 A | 1/1992 | Sancoff et al. |
| 5,088,981 A | 2/1992 | Howson et al. |
| 5,100,380 A | 3/1992 | Epstein et al. |
| 5,208,762 A | 5/1993 | Charhut et al. |
| 5,253,361 A | 10/1993 | Thurman et al. |
| 5,291,399 A | 3/1994 | Chaco |
| 5,292,029 A | 3/1994 | Pearson |
| 5,314,243 A | 5/1994 | McDonald et al. |
| 5,319,543 A | 6/1994 | Wilhelm |
| 5,367,555 A | 11/1994 | Isoyama |
| 5,376,070 A | 12/1994 | Purvis et al. |
| 5,390,236 A | 2/1995 | Klausner et al. |
| 5,395,320 A | 3/1995 | Padda et al. |
| 5,455,851 A | 10/1995 | Chaco et al. |
| 5,456,691 A | 10/1995 | Snell |
| 5,458,123 A | 10/1995 | Unger |
| 5,465,082 A | 11/1995 | Chaco |
| 5,485,408 A | 1/1996 | Blomquist |
| 5,490,610 A | 2/1996 | Pearson |
| 5,505,696 A | 4/1996 | Miki |
| 5,529,063 A | 6/1996 | Hill |
| 5,539,836 A | 7/1996 | Babkin |
| 5,542,420 A | 8/1996 | Goldman et al. |
| 5,547,470 A | 8/1996 | Johnson et al. |
| 5,562,621 A | 10/1996 | Claude et al. |
| 5,573,506 A | 11/1996 | Vasko |
| 5,582,593 A | 12/1996 | Hultman |
| 5,594,786 A | 1/1997 | Chaco et al. |
| 5,597,995 A | 1/1997 | Williams et al. |
| 5,658,250 A | 8/1997 | Blomquist et al. |
| 5,683,367 A | 11/1997 | Jordan et al. |
| 5,697,899 A | 12/1997 | Hillman et al. |
| 5,700,998 A | 12/1997 | Palti |
| RE35,743 E | 3/1998 | Pearson |
| 5,732,401 A | 3/1998 | Conway |
| 5,781,442 A | 7/1998 | Engleson et al. |
| 5,788,669 A | 8/1998 | Peterson |
| 5,793,861 A | 8/1998 | Haigh |
| 5,795,327 A | 8/1998 | Wilson et al. |
| 5,797,515 A | 8/1998 | Liff et al. |
| 5,803,917 A | 9/1998 | Butterfield et al. |
| 5,813,972 A | 9/1998 | Nazarian et al. |
| 5,814,015 A | 9/1998 | Gargano et al. |
| 5,822,418 A | 10/1998 | Yacenda et al. |
| 5,822,544 A | 10/1998 | Chaco et al. |
| 5,827,223 A | 10/1998 | Butterfield |
| 5,842,976 A | 12/1998 | Williamson |
| 5,848,593 A | 12/1998 | McGrady et al. |
| 5,848,988 A | 12/1998 | Davis |
| 5,852,590 A | 12/1998 | De La Huerga |
| 5,855,550 A | 1/1999 | Lai et al. |
| 5,865,745 A | 2/1999 | Schmitt et al. |
| 5,883,576 A | 3/1999 | De La Huerga |
| 5,885,245 A | 3/1999 | Lynch et al. |
| 5,895,371 A | 4/1999 | Levitas et al. |
| 5,903,889 A | 5/1999 | de la Huerga et al. |
| 5,912,818 A | 6/1999 | McGrady et al. |
| 5,913,197 A | 6/1999 | Kameda |
| 5,923,018 A | 7/1999 | Kameda et al. |
| 5,924,074 A | 7/1999 | Evans |
| 5,935,099 A | 8/1999 | Peterson et al. |
| 5,939,699 A | 8/1999 | Perttunen et al. |
| 5,941,846 A | 8/1999 | Duffy et al. |
| 5,943,633 A | 8/1999 | Wilson et al. |
| 5,945,651 A | 8/1999 | Chorosinski et al. |
| 5,960,085 A | 9/1999 | De La Huerga |
| 5,961,487 A | 10/1999 | Davis |
| 5,971,593 A | 10/1999 | McGrady |
| 5,993,046 A | 11/1999 | McGrady et al. |
| 6,003,006 A | 12/1999 | Colella et al. |
| 6,009,333 A | 12/1999 | Chaco |
| 6,018,713 A | 1/2000 | Coli et al. |
| 6,021,392 A | 2/2000 | Lester et al. |
| 6,024,539 A | 2/2000 | Blomquist |
| 6,032,155 A | 2/2000 | De La Huerga |
| 6,039,251 A | 3/2000 | Holowko et al. |
| 6,053,887 A | 4/2000 | Levitas et al. |
| 6,055,458 A | 4/2000 | Cochran et al. |
| 6,150,942 A | 11/2000 | O'Brien |
| 6,152,364 A | 11/2000 | Schoonen et al. |
| 6,189,727 B1 | 2/2001 | Shoenfeld |
| 6,241,704 B1 | 6/2001 | Peterson et al. |
| 6,283,322 B1 | 9/2001 | Liff et al. |
| 6,292,698 B1 | 9/2001 | Duffin et al. |
| 6,317,719 B1 | 11/2001 | Schrier et al. |
| 6,321,203 B1 | 11/2001 | Kameda |
| RE37,531 E | 1/2002 | Chaco et al. |
| 6,347,329 B1 | 2/2002 | Evans |
| 6,352,200 B1 | 3/2002 | Schoonen et al. |
| 6,363,282 B1 | 3/2002 | Nichols et al. |
| 6,364,834 B1 | 4/2002 | Reuss et al. |
| 6,408,330 B1 | 6/2002 | DeLaHuerga |
| 6,434,569 B1 | 8/2002 | Toshimitsu et al. |
| 6,449,927 B2 | 9/2002 | Hebron et al. |
| 6,464,667 B1 | 10/2002 | Kamen et al. |
| 6,475,146 B1 | 11/2002 | Frelburger et al. |
| 6,477,424 B1 | 11/2002 | Thompson et al. |
| 6,519,569 B1 | 2/2003 | White et al. |
| 6,544,228 B1 | 4/2003 | Heitmeier |
| 6,779,024 B2 | 8/2004 | DeLaHuerga |
| 6,790,198 B1 | 9/2004 | White et al. |
| 6,796,956 B2 | 9/2004 | Hartlaub et al. |
| 6,958,706 B2 | 10/2005 | Chaco et al. |
| 6,969,369 B2 | 11/2005 | Struble |

U.S. Patent    Aug. 31, 2010    US 6,790,198 C1S
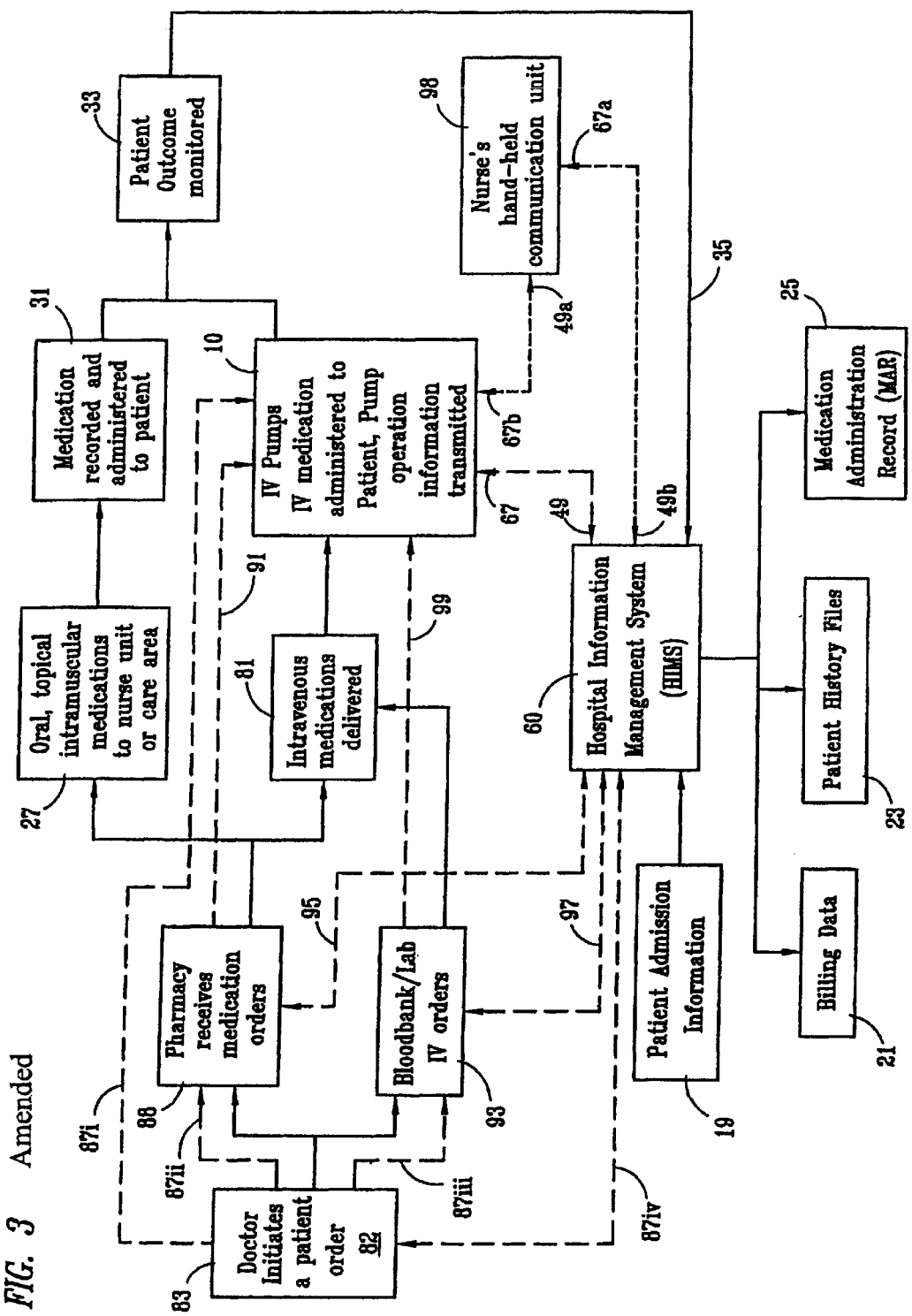
FIG. 3  Amended

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, line 12:

*This patent contains subject matter related to the subject matter in the following applications or patents, which are assigned to a common assignee; "Patient Medication IV Delivery Pump With Wireless Communication to a Hospital Information Management System", application Ser. No. 10/799,842, filed on Mar. 13, 2004, and issued as U.S. Pat. No. 7,645,258 on Jan. 12, 2010, and subject to a terminal disclaimer from this patent; and "Patient Medication IV Delivery Pump With Wireless Communication to a Hospital Information Management System", application Ser. No. 12/428,254, filed Apr. 22, 2009 as a divisional application continuing from application Ser. No. 10/799,842.*

THE DRAWING FIGURES HAVE BEEN CHANGED AS FOLLOWS:

In FIG. 3 erroneous word "pimp" is corrected to read "pump".

AS A RESULT OF REEXAMINATION, IT HAS BEEN DETERMINED THAT:

Claims 1, 2, 7, 11, 12, 15 and 16-21 are determined to be patentable as amended.

Claims 3-6, 8-10, 13 and 14, dependent on an amended claim, are determined to be patentable.

New claim 22 is added and determined to be patentable.

1. An IV medication infusion pump for use with a hospital information management system (HIMS), said IV pump comprising:

(a) pump operation circuitry [coupled with] *in* said *IV medication* infusion pump *for operating said IV medication infusion pump and* for *continuously* monitoring preselected characteristics of current infusion pumping operation;

(b) a wireless signal transmitter connected *in said IV medication infusion pump* to said pump operation circuitry for *continuously* transmitting at least one wireless signal representing said preselected current pumping operation characteristics *during pump operation*; and (c) a receiver capable of receiving said at least one wireless signal representing said current pumping operation characteristics, said receiver connected to said hospital information management system (HIMS) for receiving said current pumping operation characteristics represented by said at least one wireless signal from said IV pump.

2. The IV pump of claim 1 wherein:

(a) said operation circuitry comprises circuitry monitoring a plurality of current pumping operation characteristics selected from among rate of pumping, pumping pressure, start time, time of pumping, volume of pumping, dosage, size of tubing, speed of pumping motor, door closed, manual [programing] *programming* mode, automatic [programing] *programming* mode, start-up testing, dosage of infusion and bolus of infusion; and (b) said at least one wireless signal comprises one or more wireless signals indicative of said plurality of current pumping operation characteristics of said IV pump.

7. The IV pump of claim [1] *6* wherein:

[(a)] said pump alarm condition detection circuitry further comprises circuitry to detect at least one pump alarm condition selected from among conditions of an invalid operator ID, an invalid patient ID, a door open condition, a high pressure condition, a flow blocked condition, an air in the line condition, a low voltage condition, a pump malfunction condition, and a pump stopped condition[; and (b) said at least one wireless signal comprises a signal indicative of said at least one selected alarm condition of said IV pump].

11. The IV pump of claim 1 wherein:

(a) said operation circuitry comprises advanced end of infusion warning circuitry [programable] *programmable* for providing a warning at a selected time in advance of said end of infusion; and (b) said at least one wireless signal comprises a signal indicative of said end of infusion warning of said IV pump transmitted said selected time in advance of the end of infusion.

12. The IV pump of claim 1 wherein:

(a) said operation circuitry comprises pump operation log circuitry; and (b) said [at least one] wireless signal [comprises a signal] *transmitter is connected in said IV medication infusion pump to said pump operation log circuitry for transmitting another wireless signal representing said pump operation log* for downloading said operational log of said IV pump to said HIMS.

15. The IV pump of claim 1 wherein:

(a) said wireless signal transmitter connected to said pump operation circuitry comprise a transceiver for both transmitting at least one wireless signal representing said preselected pumping operation characteristics and for receiving input signals from said HIMS; and (b) said receiver connected to said hospital information management system (HIMS) comprises a transceiver capable of both receiving said at least one wireless signal representing said pumping operation characteristics and transmitting at least one input signal for providing at least one pumping operation parameter to said IV pump operation circuitry*; and*

*(c) said pump operation circuitry comprises user authorization code input circuitry at the IV pump, wherein said user authorization code is required prior to input of said preselected pumping operation characteristics represented by said input wireless signal from said HIMS.*

16. A wireless communication system from an IV medication infusion pump to a hospital information management system (HIMS) comprising:

(a) pump operation circuitry [coupled with] *in* said IV medication infusion pump *for operating said IV medication infusion pump and* for monitoring preselected characteristics of current infusion pumping operation;

(b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;

(c) a wireless signal pump transmitter connected to said pump operation circuitry for transmitting at least one wireless signal representing said preselected monitored current pumping operation characteristics;

(d) an HIMS receiver capable of receiving said at least one wireless signal representing said pumping operation characteristics, said receiver connected to said hospital information management system (HIMS) for receiving said current pumping operation characteristics represented by said at least one wireless signal from said IV pump, said HIMS receiver further capable of receiving said signal representing said doctor's order; [and]

(e) wherein said HIMS further comprises [programing] *programming* for receiving, storing and comparing said pump signal with said signal representing said doctor's order to determine whether said medication is delivered to said patient by operation of said pump according to said doctor's order; *and*

*(f) wherein said operation circuitry comprises user authorization code input circuitry at the IV pump wherein a user authorization code is required to be input at said pump prior to uploading said doctor's order provided by said signal representing said doctor's order received from said HIMS and further comprising a display of said doctor's order and the comparison by said HIMS and circuitry requiring manual validation of said doctor's orders for pump operation prior to uploading at said IV pump and requiring manual activation of said pump operation following said display of said wirelessly transmitted doctor's order and comparison.*

17. A wireless communication system from an IV medication infusion pump to a hospital information management system (HIMS) as in claim 16 further comprising:

(a) a pharmacy receiver for receiving said doctor's order signal representing said doctor's order, said pharmacy receiver operatively connected to a program and a display to provide human readable information sufficient for a pharmacist to prepare the ordered medication;

(b) a pharmacy transmitter for sending a delivery signal indicating that an IV medication has been delivered to a nurses station and representing that the IV medication is to be administered to a patient according to said doctor's order; [and]

(c) wherein said HIMS further comprises [programing] *programming* for storing said delivery signal and for comparing said delivery signal to said order signal and/or to said pump operation characteristics signal to facilitate monitoring of the timely delivery of the IV medication to the patient according to the doctor's order *and to provide a wireless signal received and displayed at the pump representing the order signal;*

*(d) wherein the authorization code is required to be input at the pump prior to uploading said wireless doctor's order signal at the pump from said HIMS; and*

*(e) said operation circuitry comprises validation circuitry requiring manual validation of said doctor's order and said pump operation characteristics, and activation circuitry requiring manual activation of said pump operation at the IV pump following said display of said wirelessly transmitted doctor's order signal from said HIMS.*

18. A wireless communication system from an IV medication infusion pump to a hospital information management system (HIMS) as in claim 16 further comprising:

(a) laboratory receiver for receiving said order signal when a blood product IV is ordered fo the patient; and (b) a laboratory signal transmitter for signaling to said HIMS the delivery of a blood product IV for administration to a [patent] *patient* and including information related to the time sensitivity of the blood product;

(c) wherein said HIMS further comprises [programing] *programming* for comparing said laboratory signal to said pump [parameter] *operation characteristics* signal so that actual timely delivery of said blood product represented by said laboratory signal can be monitored and the results of the comparison can be displayed, *and to provide a wireless signal received and displayed at the IV pump representing the laboratory signal;*

*(d) wherein the authorization code is required prior to uploading said laboratory signal provided by said at least one wireless signal from said HIMS representing the comparison of the laboratory signal; and*

*(e) said operation circuitry comprises validation circuitry requiring manual validation of said laboratory signal and said pump operation characteristics signal, and activation circuitry requiring manual activation of said pump operation at the IV pump following said display of said wirelessly transmitted laboratory signal from said HIMS.*

19. A wireless communication system from an IV medication infusion pump to a hospital information management system (HIMS) as in claim 16 wherein:

(a) said transmitter connected to said pump comprises a transceiver for receiving signals corresponding to pumping operation characteristics according to said doctor's order for medication to a patient; [and]

(b) said HIMS receiver comprises a transceiver for receiving said doctor's order and for transmitting another signal representing pumping operation characteristics corresponding to said doctor's ordered medication for a patient, *and to provide a wireless signal received and displayed at the IV pump representing the pumping operation characteristics according to said doctor's order signal;*

*(c) wherein the authorization code is required prior to downloading said pumping operation characteristics according to said doctor's order signal and the pump operation characteristic signal provided by said at least one wireless signal from said HIMS and further comprising a display of said doctor's order; and*

*(d) said operation circuitry comprises validation circuitry requiring manual validation of said pumping operation characteristics according to said doctor's order, and activation circuitry requiring manual activation of said pump operation at the IV pump following said display of said wirelessly transmitted pumping operation characteristics according to said doctor's order signal.*

20. A wireless communication system from an IV medication infusion pump to a hospital information management system (HIMS) as in claim 16 further comprising:

(a) a nurses station transmitter having an input for entry of information on IV medication received at a nurses station and for transmitting a medicine received signal representing the IV medications received for a patient upon receiving any ordered medication; [and]

(b) wherein said HIMS further comprises [programing] *programming* for receiving and storing said IV medication received signal and for comparing said medication received signal with at least one of said order signal and said pumping characteristic signal to facilitate monitoring of preparation, delivery and administration of said IV medication and for providing the results *and to provide a wireless signal received and displayed at the IV pump representing the IV medication received signal;*

(c) *wherein the authorization code is required prior to downloading said IV medication received signal provided by said at least one wireless signal from said HIMS and further comprising a display of said IV medication received signal; and*

(d) *said operation circuitry comprises validation circuitry requiring manual validation of said IV medication received signal, and activation circuitry requiring manual activation of said pump operation at the IV pump following said display of said wirelessly transmitted IV medication received signal.*

21. A wireless communication system from an IV medication infusion pump to a hospital information management system (HIMS) comprising:

(a) a medication order transmitted capable of receiving input of a doctor's order for patient medication to be administered with an IV pump and capable of wireless transmission of a first signal representing the input order for said patient medication for IV administration;

(b) an IV pump having pump operation circuitry for monitoring preselected characteristics of pump operation and a transmitter connected to said pump operation circuitry for transmitting a second wireless signal representing said preselected pump operation characteristics indicative of *current* IV administration of medication to a patient;

(c) a receiver for receiving said first signal and for providing said order for patient medication in human readable form for the preparation of said ordered patient medication for IV pump administration; [and]

(d) a hospital information management system including a receiver capable of receiving said first and said second signals and a computer processor capable of storing said information represented by said signals, capable of comparing said doctor's order for patient medication to said IV pump delivery of medication to a patient and for comparing said order to said [delivery] *current administration* characteristics to determine whether medication delivery was as ordered by the doctor and for displaying said order and said pump operation characteristics and the results of the comparison thereof *and to provide a third wireless signal received and displayed at the IV pump representing a confirmed doctor's order for medication to be delivered;*

(e) *wherein said operation circuitry comprises user authorization code input circuitry at the IV pump, wherein an authorization code is required prior to downloading said confirmed doctor's order for delivery provided by said third wireless signal from said HIMS representing the confirmed doctor's order signal and further comprising a display of said confirmed doctor's order for medication to be delivered; and*

(f) *said operation circuitry comprises validation circuitry requiring manual validation of said confirmed doctor's order for patient medication for IV administration, and activation circuitry requiring manual activation of said pump operation at the IV pump following said display of said wirelessly transmitted confirmed doctor's order for patient medication for IV administration.*

22. *An IV medication infusion pump for use with a hospital information management system (HIMS), said IV pump comprising:*

(a) *pump operation circuitry in said infusion pump;*

(b) *monitoring circuitry integrally formed with said pump operation circuitry connected in said pump for continuously monitoring preselected characteristics of current infusion pumping operation;*

(c) *a wireless signal transmitter connected to said pump and electrically connected in said pump to said integrally formed pump operation circuitry and monitoring circuitry for continuously transmitting at least one wireless signal representing said preselected current pumping operation characteristics; and*

(d) *a receiver capable of receiving said at least one wireless signal representing said current pumping operation characteristics, said receiver connected to said hospital information management system (HIMS) for receiving said current pumping operation characteristics represented by said at least one wireless signal from said IV pump.*

\* \* \* \* \*